(12) United States Patent
Blomqvist

(10) Patent No.: US 9,026,207 B2
(45) Date of Patent: May 5, 2015

(54) MEDICAL DEVICE FOR ATRIAL FIBRILLATION PREDICTION

(75) Inventor: Andreas Blomqvist, Spånga (SE)

(73) Assignee: St Jude Medical AB, Jarfalla (SE)

(*) Notice: Subject to any disclaimer, the term of this patent is extended or adjusted under 35 U.S.C. 154(b) by 815 days.

(21) Appl. No.: 12/810,406

(22) PCT Filed: Jan. 28, 2008

(86) PCT No.: PCT/SE2008/000078
§ 371 (c)(1),
(2), (4) Date: Jun. 24, 2010

(87) PCT Pub. No.: WO2009/096820
PCT Pub. Date: Aug. 6, 2009

(65) Prior Publication Data
US 2010/0280394 A1    Nov. 4, 2010

(51) Int. Cl.
| | | |
|---|---|---|
| *A61N 1/365* | (2006.01) | |
| *A61B 5/02* | (2006.01) | |
| *A61B 5/0205* | (2006.01) | |
| *A61B 5/0452* | (2006.01) | |
| *A61B 5/053* | (2006.01) | |
| *A61B 5/08* | (2006.01) | |
| *A61B 5/00* | (2006.01) | |
| *A61N 1/362* | (2006.01) | |

(52) U.S. Cl.
CPC ........... *A61N 1/36521* (2013.01); *A61B 5/0031* (2013.01); *A61B 5/02028* (2013.01); *A61B 5/0205* (2013.01); *A61B 5/0452* (2013.01); *A61B 5/053* (2013.01); *A61B 5/0809* (2013.01); *A61B 5/4818* (2013.01); *A61N 1/3622* (2013.01); *A61B 5/7239* (2013.01)

(58) Field of Classification Search
USPC ..................... 600/533, 547; 607/18
See application file for complete search history.

(56) References Cited

U.S. PATENT DOCUMENTS

| | | | | |
|---|---|---|---|---|
| 5,951,593 | A * | 9/1999 | Lu et al. ........................ | 607/14 |
| 7,162,294 | B2 * | 1/2007 | Rowlandson et al. ........ | 600/513 |
| 7,190,996 | B2 | 3/2007 | Järverud | |
| 7,200,440 | B2 * | 4/2007 | Kim et al. ..................... | 607/18 |
| 2004/0059240 | A1 | 3/2004 | Cho et al. | |
| 2004/0133123 | A1 * | 7/2004 | Leonhardt et al. ............ | 600/547 |
| 2005/0234313 | A1 | 10/2005 | Rowlandson et al. | |

(Continued)

FOREIGN PATENT DOCUMENTS

WO    WO 2007/038861    4/2007

OTHER PUBLICATIONS

"Prevalence of Sleep Apnea Syndrome in Lone Atrial Fibrillation: A Case-control Study," Porthan et al., CHEST, vol. 125 (2004) pp. 879-885.

(Continued)

*Primary Examiner* — Kennedy Schaetzle

(57) ABSTRACT

In a device and a method for providing correlated measures for predicting potential occurrence of atrial fibrillation, an impedance of the patient is measured to obtain impedance information; cardiogenic data is determined from the information; respiratory data is determined from the information; at least one hemodynamic measure is calculated from the cardiogenic data and at least one apnea measure is calculated from the respiratory data; the hemodynamic and apnea measures are correlated such that the correlated measures can be utilized for predicting potential occurrence of atrial fibrillation.

18 Claims, 13 Drawing Sheets

(56) References Cited

U.S. PATENT DOCUMENTS

| | | | |
|---|---|---|---|
| 2007/0032733 A1* | 2/2007 | Burton | 600/509 |
| 2007/0118180 A1 | 5/2007 | Ni et al. | |
| 2007/0265539 A1* | 11/2007 | Hastings et al. | 600/513 |

OTHER PUBLICATIONS

"The Risk Profile for Obstructive Sleep Apnea Does Not Affect the Recurrence of Atrial Fibrillation," Padeletti et al., PACE, vol. 29, No. 7 (2006) pp. 727-732.

"Association of Atrial Fibrillation and Obstructive Sleep Apnea," Gami et al., Circulation, vol. 110, (2004) pp. 364-367.

"Atrial Fibrillation Reduces the Atrial Impedance Amplitude During Cardiac Cycle: A Novel Detection Algorithm to Improve Recognition of Atrial Fibrillation in Pacemaker Patients," Schmidt et al., Europace, vol. 9 (2007) pp. 812-816.

"Activation Delay After Premature Stimulation in Chronically Diseased Human Mvocardium Relates to the Architecture of Interstitial Fibrosis," Kawara et al., http://circ.ahajournals.org/cgi/content/full/104/25/3069 pp. 3069-3075.

* cited by examiner

MEDICAL DEVICE FOR ATRIAL FIBRILLATION PREDICTION

BACKGROUND OF THE INVENTION

1. Field of the Invention

The present invention generally relates to implantable medical devices, such as cardiac pacemakers, and in particular to the monitoring of parameters useful for the prediction of atrial fibrillation.

2. Description of the Prior Art

Atrial fibrillation (AF) is a cardiac arrhythmia, i.e. a an altered electrical activity (irregular or faster or slower than normal) of the heart, that involves the atria. AF may be detected as irregularities when taking a pulse. AF is the most common form of arrhythmia affecting approximately 3-5% of people over 65 and 8% of people over 80. For example, there are about 2.2 million cases in the U.S. yearly.

In AF, the electrical impulses that are normally generated by the sinoatrial node (the sinus node) are replaced by disorganized activity in the atria, leading to irregular conduction of impulses to the ventricles that generate the heartbeat. This results in irregular heartbeats. AF may be continuous (persistent or permanent AF) or alternating between periods of normal heart rhythm (paroxysmal AF). Over time, the natural tendency of AF is to become continuous/chronic. The type of AF considered to be most dangerous is, perhaps a bit surprising, paroxysmal AF because the recurrent onsets and offsets of fibrillation increases the probability of embolization significantly. During an AF episode, the blood is rather stationary in the atria and coagulation forming blood clots may take place. When the activity then returns to normal, the clots are propelled out into the system, potentially causing strokes etc. Further, paroxysmal AF is the type of AF that normally occurs first, i.e. it is rather unusual that a healthy subject immediately enters chronic AF. As the first type of AF to hit a subject usually is the most dangerous one, it is desirable to predict AF before it actually starts.

In US 2005/0234313, a system and a method for determining a correlation between sleep apnea and sudden cardiac death is disclosed. "Sudden cardiac death" (SCD) is defined as death within one hour of the onset of symptoms without a previously-known disease or without symptoms. It is described that SCD may be predicted in a patient being monitored for sleep apnea by acquisition of respiration data, by means of e.g. impedance, and electrocardiogram (ECG) data, to determine the correlation. The methods of the disclosure are non-invasive procedures.

In EP 1384433, a monitor for early detection of an ischemic heart disease of a patient is disclosed. The invention relies on impedance measurements and the detection of a notch in an impedance signal. It is described that a parameter defined as $\Delta Z_1/\Delta Z_2$ may be used to detect an ischemic condition, such as e.g. AF, wherein $\Delta Z_1$ denotes the difference between a maximum value of the measured impedance and the impedance value measured in a plateau occurring in the impedance curve after the notch, and $\Delta Z_2$ the difference between the impedance value in the plateau and a minimum value of the measured impedance in an impedance decrease following the plateau.

In WO 2007/038861, a device for predicting potential occurrence of atrial fibrillation is disclosed. The device comprises an input unit for receiving at least one heart activity signal, and a processing unit for deriving data regarding a plurality of cardiac parameters and determining a likelihood of occurrence of atrial fibrillation based on a correlation between at least two of the cardiac parameters. The cardiac parameters disclosed are conduction times, i.e. time intervals between the activation of a first and a second electrode.

However, there remains a need within the art for an improved device and method for early and convenient prediction of AF.

SUMMARY OF THE INVENTION

It is an object of the present invention to meet this need by the provision an implantable medical device and a method for providing measures useful for prediction of AF.

It is another object of the present invention to provide a medical system, including an implantable medical device and an extracorporeal programmer apparatus, for providing measures useful for prediction of AF.

According to an aspect of the present invention, there is provided an implantable medical device including a pulse generator adapted to produce cardiac stimulating pacing pulses, the device being connectable to at least one medical lead comprising electrodes for delivering the pulses to cardiac tissue of a heart of a patient, comprising: an impedance measuring unit, connectable to at least two electrodes of the at least one medical lead, adapted to measure an impedance of the patient and provide impedance information corresponding to the measured impedance; a cardiogenic impedance determining unit adapted to receive the impedance information and determine cardiogenic impedance data from the impedance information; a respiration impedance determining unit adapted to receive the impedance information and determine respiratory impedance data from the respiratory impedance information; a calculation unit adapted to determine at least one hemodynamic measure using the cardiogenic impedance data and at least one apnea measure using the respiratory impedance data; and a correlating unit adapted to receive the hemodynamic and apnea measures and correlate the hemodynamic and apnea measures, wherein the correlated hemodynamic and apnea measures can be utilized for predicting potential occurrence of atrial fibrillation.

According to a second aspect of the invention, there is provided a medical system including an extracorporeal programmer apparatus, comprising an extracorporeal communication unit and an implantable medical device including a pulse generator adapted to produce cardiac stimulating pacing pulses, the device being connectable to at least one medical lead comprising electrodes for delivering the pulses to cardiac tissue of a heart of a patient, an internal communication unit adapted to communicate with the extracorporeal communication unit, and an impedance measuring unit, connectable to at least two electrodes, adapted to measure an impedance of the patient over at least one consecutive heart event and provide impedance information corresponding to the measured impedance, wherein the system further comprises: a cardiogenic impedance determining unit adapted to receive the impedance information provided by the impedance measuring unit and determine cardiogenic impedance data from the impedance information and a respiration impedance determining unit adapted to receive the impedance information provided by the impedance measuring unit and determine respiratory impedance data from the respiratory impedance information; a calculation unit adapted to receive the respiratory and cardiogenic impedance data and determine at least one hemodynamic measure using the cardiogenic impedance data and at least one apnea measure using the respiratory impedance data; and a correlating unit adapted to receive the hemodynamic and apnea measures and correlate the hemodynamic and apnea measures, wherein the correlated hemodynamic and apnea measures can be utilized for predicting potential occurrence of atrial fibrillation.

According to a third aspect of the invention, there is provided a method for providing correlated measures for predicting potential occurrence of atrial fibrillation, that includes the steps of: measuring an impedance of the patient to obtain impedance information; determining cardiogenic data from the information; determining respiratory data from the information; calculating at least one hemodynamic measure from a cardiogenic data and at least one apnea measure from the respiratory data; and correlating the hemodynamic and apnea measures such that the correlated hemodynamic and apnea measures can be utilized for predicting potential occurrence of atrial fibrillation.

According to a fourth aspect of the invention, there is provided a computer program product, comprising software code portions for performing steps in accordance with the method aspect (third aspect) of the invention.

According to a fifth aspect of the invention, there is provided a computer readable medium comprising instructions for bringing a computer to perform steps in accordance with a method aspect of the invention.

Thus, the present invention is based on the insight that there is a link between sleep apnea and atrial fibrosis, and that by monitoring these two conditions, AF may be predicted at an early stage.

In Porthan et al. *Chest*, 2004, vol. 125, p. 879-85, it is examined whether there is a prevalence of sleep apnea syndrome (SAS) in AF, and the authors conclude that SAS could not be shown to be more common in patients with AF than in a control group. Further, in Padeletti et al., *PACE*, 2006, vol. 29, iss. 7, p. 727-32, it is shown that the prevalence paroxysmal AF was similar in a patient group of high risk for obstructive sleep apnea (OSA) and in a patient group of low risk for OSA. However, in Gami et al., *Circulation*, 2004, vol. 110, p. 364-7, the authors state that there is a strong association between OSA and AF, such that OSA is more common in patients with AF than in high-risk patients with other cardiovascular diseases. Consequently, the connection between sleep apnea and AF is debated within the art.

The inventor's insight is that disordered breathing, e.g. during sleep, will lead to less oxygenated blood than what the body needs, and subsequently, that the decrease in oxygen saturation may lead to minor ischemic events, or anoxia, in the atrial tissue, causing (increased) atrial fibrosis, i.e. fibrous tissue in the myocardium of the atria. Furthermore, atrial fibrosis has been suggested to be involved in the development of AF (T. Kawara et al. *Circulation*, 2001, vol. 104, iss. 25, p. 3069-75).

According to the above, just monitoring sleep apnea seems to be insufficient for accurately detecting or predicting AF. However, by taking advantage of the link between sleep apnea and atrial fibrillation, and simultaneously monitoring these two conditions, a subgroup of sleep apnea patients having an increased risk of developing AF may be identified at an early stage. In other words, by detecting an increasing apnea activity coinciding with development of atrial fibrosis, AF may be predicted. Having in mind that paroxysmal AF is normally the type of AF to affect a patient, the invention may be particularly useful for predicting paroxysmal AF.

Further, the inventor has found that the monitoring of both these conditions may conveniently be achieved by means of invasive impedance measurements using an implantable device.

A breathing pattern of a patient may be derived from impedance information corresponding to impedance measured by a device implanted in the patient. The physical movements corresponding to breaths during normal breathing give rise to regular changes in the measured impedance. A pattern of these changes, i.e. a breathing contribution to the measured impedance, may be extracted from the corresponding impedance information and used for monitoring breathing activity. Irregularities in such pattern may indicate apnea activity and may be used in the calculation of the apnea measure.

An elasticity of the myocardium of the atria may be monitored by means of impedance information corresponding to an impedance, particularly a cardiogenic impedance substantially corresponding to an impedance of an atrium of a patient, measured by a device implanted in the patient. For example, a decreased elasticity may present as a slower filling process of an atrium of the patient, which may be detected by means of impedance because blood is a better electrical conductor than the tissue of the heart. As mentioned above, atrial fibrosis is fibrous tissue in the myocardium of the atria, and the fibrous tissue may decrease the elasticity of the atrial myocardium of the patient. Consequently, the elasticity of the atrial myocardium may reveal the atrial fibrosis status. In general, a decreased elasticity of the atrial myocardium corresponds to an aggravated atrial fibrosis. Further, the fibrous tissue in itself may be detected by impedance. In such case, the impedance information and/or the impedance data may include the phase angle of the complex impedance. In conclusion, the hemodynamic measure of the present invention may correspond to any measure showing the atrial fibrosis status of the patient. For example, the hemodynamic measure may be any measure corresponding to an elasticity of the atrial myocardium of a patient.

Consequently, according to the invention, at least one impedance signal is used in the determination of both a hemodynamic measure giving information about the atrial fibrosis status of the patient and an apnea measure giving information about the apnea activity of the patient.

In the context of the present disclosure, "to correlate", or "correlating", the hemodynamic and apnea measures, refers to bringing them into a relationship. For example, the hemodynamic and apnea measures may be presented on a common time axis to show their respective progression over time. From such a presentation, a person, such as a physician, may not only observe occurrences of apneic events (involuntary breathing pauses) as well as atrial fibrosis information, but may also be able to compare the development of the two parameters. As an example, an increasing apnea activity coinciding with a decreasing elasticity of the atrial myocardium, indicates an increasing risk for developing AF.

Consequently, in one embodiment of the present invention, the correlating unit may be further adapted to correlate said hemodynamic and apnea measures such that an increasing apnea activity coinciding with a decreasing elasticity of the atrial myocardium may be detected by a person studying the correlated measures. For example, the apnea activity may be a frequency of apneic events.

In one embodiment of the present invention, the correlating unit may be further adapted to calculate an AF prediction value for the patient utilizing the hemodynamic and apnea measures, wherein the AF value can be used for predicting potential occurrence of AF. Consequently, the relationship between the measures may be quantified. As an example, the AF prediction value may be calculated as $$R = -m^*\alpha + n^*\beta,$$

wherein R is the AF prediction value, $\alpha$ is the hemodynamic measure, $\beta$ is the apnea measure, n and m are positive constants, an increasing atrial fibrosis, e.g. represented by a decreasing elasticity of the myocardium, results in a decreasing $\alpha$, and an increasing apnea activity, such as an increasing number of apneic events, results in an increasing $\beta$. Consequently, an increasing R corresponds to an increasing risk of developing AF. As an example, a reference value ($R_{ref}$) may be provided, and when $R>R_{ref}$, the risk for developing AF may be considered to be serious, which may in turn lead a physician to treat or supervise the patient.

However, the AF prediction value may also be any other function of $\alpha$ and $\beta$ which provides relevant information about the risk of developing AF.

In another embodiment of the present invention, the impedance measuring unit may be adapted to measure a cardiogenic impedance substantially corresponding to an impedance of an atrium, e.g. the left atrium and/or right atrium, of the patient. Such measurements may be achieved by using various combinations of electrodes arranged in various positions within the patient, especially within the heart of the patient. As an example, the measuring unit may be adapted to measure an impedance between a left ventricular coronary sinus lead and a right atrial lead. As another example, the measuring unit may be adapted to perform the impedance measurements by means of a current which is sent out between an $RA_{ring}$ (i.e. a proximal ring electrode of a medical lead, which electrode is arranged in the right atrium) and a case of the implantable medical device (i.e. a conductive housing of the implantable medical device) and a voltage which is measured between an $RA_{ring}$ and an $LV_{ring}$ (i.e. a proximal ring electrode of a medical lead, which electrode is arranged adjacent to the left ventricle). As yet another example, the measuring unit may be adapted to perform the impedance measurements by means of a current which is sent out between an $RA_{ring}$ and an $LV_{ring}$ and a voltage which is measured between an $RA_{ring}$ and an $LV_{ring}$.

Preferably, the impedance measuring unit adapted to measure a cardiogenic impedance substantially corresponding to an impedance of an atrium is further adapted to perform such measurements such that a change in the cardiogenic impedance corresponding to a decreased elasticity of the myocardium of the atrium may be detected by the implantable medical device. This may be achieved in different ways, e.g. by measuring the impedance of an atrium being filled with blood, or by measuring the impedance of the myocardial tissue of the atrium.

By looking at the complex impedance including the phase angle, tissue characteristics of the heart of the patient may be detected. Consequently, in another embodiment of the present invention, the impedance measuring unit may be adapted to measure a cardiogenic impedance substantially corresponding to the atrial myocardium and the calculation unit may be adapted to determine the hemodynamic measure by means of impedance data based on measured complex impedance including phase angle.

In another embodiment of the present invention, the calculation unit is adapted to determine the at least one hemodynamic measure by means of a time derivative of a cardiogenic impedance curve formed by means of the cardiogenic impedance data, wherein each determined time derivative corresponds to a change of the cardiogenic impedance during a cardiac cycle. Actions of a heart may be monitored by analyzing changes in an impedance of the heart. Filling and ejection of atria and ventricles are examples of heart actions that give rise to impedance changes because blood is a better electrical conductor than the tissue of the heart. By looking at time derivatives of an obtained impedance curve, the speed of such actions may be detected. Further, the decreased elasticity of the myocardium in atrial fibrosis may slow down such actions. Consequently, atrial fibrosis may be detected by means of derivatives of impedance curves.

The atrial filling is preceded by electrical activity in the heart. A QRS complex of an ECG-curve, formed by means of a ECG signal from the heart, corresponds to such electrical activity. The QRS complex may thus be utilized for measuring the change in impedance during atrial filling. Consequently, in an embodiment, the implantable medical device further includes an ECG-measuring unit, connectable to at least one electrode, adapted to receive an ECG signal from the heart, determine an ECG curve, and detect a QRS complex of the ECG curve, wherein the calculation unit is further adapted to obtain information related to the QRS complex and the ECG curve from the ECG-measuring unit, synchronize the cardiogenic impedance curve with the detected QRS complex, and calculate the time derivative in a time window following the QRS complex.

As an example, the ECG-measuring unit may be adapted to receive an intracardiac electrocardiogram signal (IECG signal), i.e. a signal detected in the heart of the patient. As an alternative, or a complementary, example, the ECG-measuring unit may be adapted to receive a ECG signal detected in an epicardial position, e.g. via a lead, such as an LV lead, arranged in a coronary vein.

In another embodiment, the calculation unit is further adapted to compare the hemodynamic measure with a hemodynamic reference value. The hemodynamic reference value may be a predetermined value. Alternatively, the hemodynamic reference value may be a measured value. For example, the calculation unit may be adapted to determine such reference value shortly after the implantable medical device is implanted in the patient, such as within a week, or within a day, of the implantation. As an example, such reference value may be calculated as an average value over a predetermined number of values or of values obtained over a predetermined period of time or as a weighted average value over a predetermined number of values or of values obtained over a predetermined period of time. By determining a reference value shortly after the implantation, it is possible to compare hemodynamic measures from later measurements with such reference values to determine if the condition of the heart worsens, e.g. if the elasticity of the myocardium decreases.

In another embodiment, the apnea measure is a number of apneic events and the calculation unit is adapted to detect a first breath from the respiratory impedance data and increase the number of apneic events if no second breath is detected from the respiratory data in a time window of a predetermined length following the first breath. Consequently, the apnea activity of the patient may be quantified by counting the number of apneic events. An apneic event is considered to have occurred if the time interval between two breaths is exceeding a predetermined value, such as at least 8 seconds, such as least 9 seconds, such as at least 10 seconds, such as at least 11 seconds, such as at least 12 seconds, such as at least 15 seconds, such as at least 20 seconds, such as at least 30 seconds. Consequently, the incidence of an apneic event may be detected by identifying a first breath and a second breath, wherein the second breath is the breath following the first, and then comparing the time between the breaths with the predetermined value. If an apneic event is detected, a counter of apneic events may be increased by one. As an example, the total number of apneic events may be stored after each night and then set to zero. Consequently, it may be possible to present the development of apneic events per night over a time period. In a complementary embodiment, the duration of each detected apneic event may also be registered. Consequently, the quantification of the apnea activity, i.e. the apnea measure, may be calculated as a function of the number of apneic events and/or the duration of these apneic events. A longer apneic event may thus give a greater contribution to the apnea measure than a shorter.

In another embodiment, the calculation unit is further adapted to detect a breath from the respiratory impedance data by means of integrating a respiratory impedance curve, formed by means of the respiratory data, to obtain a surface area value. Accordingly, in such embodiment, a respiratory impedance curve is formed from the respiratory impedance data. The respiration impedance determining unit or the calculation unit may be adapted to form the respiratory impedance curve. As an example, the surface area value of the respiratory impedance curve may be obtained by integrating the respiratory impedance curve in a time window corresponding to a substantial change in the respiratory impedance of the respiratory impedance curve. The impedance of the respiratory impedance curve may essentially correspond to the respiration of the patient. A "substantial change in the respiratory impedance of the respiratory impedance curve" may therefore reflect an inhalation or an exhalation. For example, the detection of a breath may include integration over at least part of a peak of the respiratory impedance curve to obtain the surface area value corresponding to the at least part of the peak. The detection of, and integration over, peaks of the respiratory impedance curve may be executed in accordance with well established signal processing techniques within the art.

In one embodiment, the calculation unit may be adapted to detect a breath if the surface area value is higher than a reference surface area value. The reference surface area value may be a predetermined value. Alternatively, the reference surface area value may be a measured value. For example, the calculation unit may be adapted to determine such reference value shortly after the implantable medical device is implanted in the patient. As an example, such reference value may be calculated as an average value over a predetermined number of values or of values obtained over a predetermined period of time or as a weighted average value over a predetermined number of values or of values obtained over a predetermined period of time. In one embodiment, a predetermined, preliminary reference surface area value may be used for the detection of breaths shortly after the implantation of the implantable device. Subsequently, the surface area values of the so detected breaths may be used for determining the reference surface area value. As an example, the reference surface area value may be a predetermined percentage of an average of the surfaces of the initially detected breaths. Thus, in one embodiment, the calculation unit may be adapted to determine the reference surface area value as a function of at least one measured surface area value.

In another embodiment, the implantable medical device may further include a sleep indication unit adapted to detect a sleeping state of the patient and generate sleep status information, wherein at least one component of the device is adapted to receive the sleep status information and execute a predetermined action as a result of the received sleep status information. Consequently, the performance of the device may be adapted to the sleeping status of the patient. For example, the sleep indication unit may be adapted to receive posture information from a posture sensor adapted to sense a posture of the patient, activity level information from an activity sensor adapted to sense an activity of the patient, and/or breathing information from the impedance measuring unit, the respiratory impedance information determining unit, the calculation unit or the correlating unit. The sleep indication unit may thus be adapted to detect a sleeping state based on information form one or more sensors and/or units. For example, the sleep status unit may be adapted to generate sleep status information indicating a sleeping state of the patient if receiving information indicating a lying position of the patient, an activity which is lower than a reference activity and/or a breathing pattern which corresponds to a sleeping state, such as a breathing rate which is lower than a reference rate.

In one embodiment, the impedance measuring unit may be adapted to receive the sleep status information and initiate impedance measurements if a sleeping state of the patient is indicated. Consequently, it is possible to limit the impedance measurements to the patient sleeping periods.

In another embodiment, the cardiogenic or respiratory impedance determining unit is adapted to receive the sleep status information and determine the cardiogenic or respiratory impedance data, respectively, if a sleeping state of the patient is indicated. Consequently, it is possible to limit the determinations of the cardiogenic or respiratory impedance determining units to the patient sleeping periods.

In another embodiment, the calculation unit is adapted to receive the sleep status information and determine the hemodynamic and apnea measures as a function of the sleep status information, if a sleeping state of the patient is indicated. Consequently, it is possible to limit the determination of the hemodynamic and apnea measures to the patients sleeping periods.

In another embodiment, the correlation unit is adapted to receive the sleep status information and correlate the hemodynamic and apnea measures as a function of the sleep status information, if a sleeping state of the patient is indicated. Consequently, it is possible to limit the correlating of the hemodynamic and apnea measures to the patients sleeping periods.

In an embodiment, the implantable medical device of the invention is adapted to two-way communication with an extracorporeal device, such as an extracorporeal device comprising a display device adapted to visually display the hemodynamic and apnea measures and/or the correlated the hemodynamic and apnea measures. As an example, the implantable medical device may comprise a communication unit, such as a telemetry unit, adapted to receive the hemodynamic and apnea measures and/or the correlated hemodynamic and apnea measures and transfer them to an extracorporeal device, such as an extracorporeal programmer apparatus connectable to a display device adapted to visually display the measures.

In an embodiment of the medical system according to the invention, the cardiogenic impedance determining unit may be arranged in the extracorporeal programmer apparatus. In an alternative embodiment, the cardiogenic impedance determining unit may be arranged in the implantable medical device.

In an embodiment of the medical system according to the invention, the respiratory impedance determining unit may be arranged in the extracorporeal programmer apparatus. In an alternative embodiment, the respiratory impedance determining unit may be arranged in the implantable medical device.

In an embodiment of the medical system according to the invention, the calculation unit may be arranged in the extracorporeal programmer apparatus. In an alternative embodiment, the calculation unit may be arranged in the implantable medical device.

In an embodiment of the medical system according to the invention, the correlating unit may be arranged in the extracorporeal programmer apparatus. In an alternative embodiment, the correlating unit may be arranged in the implantable medical device.

In an embodiment of the medical system according to the invention, the extracorporeal apparatus further comprises a display device adapted to visually display the hemodynamic and apnea measures and/or the correlated the hemodynamic and apnea measures. From such a display, a person, such as a physician, or the patient himself, may assess the risk of developing AF.

In an embodiment of the method according to the invention, the correlating step may comprise calculation of an atrial fibrillation prediction value for the patient utilizing the hemodynamic and apnea measures, wherein the atrial fibrillation prediction value can be utilized for predicting potential occurrence of atrial fibrillation. This is further discussed above in connection with the correlating unit.

In an embodiment of the method according to the invention, the impedance of the patient may be substantially corresponding to an impedance of an atrium, e.g. the left and/or right atrium, of the patient. This is further discussed above in connection with the impedance measuring unit.

In another embodiment of the method according to the invention, the hemodynamic measure may be calculated by means of a time derivative of a cardiogenic impedance curve formed by means of the cardiogenic impedance data, wherein each determined time derivative corresponds to a change of the cardiogenic impedance during a cardiac cycle. This is further discussed above in connection with the calculating unit.

In another embodiment of the method according to the invention, the method may further comprise the steps of: receiving an ECG signal from the heart; determining an ECG curve; and detecting a QRS complex of the ECG curve, wherein the calculating step is involving obtaining information related to the QRS complex and the ECG curve, synchronizing the cardiogenic impedance curve with the detected QRS complex, and calculating the time derivative in a time window following the QRS complex. This is further discussed above in connection with the ECG-measuring unit.

In another embodiment of the method according to the invention, the calculating step may further comprise comparing the hemodynamic measure with a hemodynamic reference value. This is further discussed above in connection with the calculation unit.

In another embodiment of the method according to the invention, the apnea measure may be a number of apneic events and the calculating step may comprise detecting a first breath from the respiratory impedance data and, if no second breath is detected from the respiratory data in a time window of a predetermined length following the first breath, increase the number of apneic events. This is further discussed above in connection with the calculation unit.

In another embodiment of the method according to the invention, the calculating step may comprise detecting a breath from the respiratory impedance data by means of integrating a respiratory impedance curve, formed by means of the respiratory data, to obtain a surface area value. This is further discussed above in connection with the calculation unit.

In another embodiment of the method according to the invention, the calculating step may comprise integrating the respiratory impedance curve in a time window thereof corresponding to a substantial change in the respiratory impedance to obtain the surface area value. This is further discussed above in connection with the calculation unit.

In another embodiment of the method according to the invention, the calculating step may comprise detecting the breath if the surface area value is higher than a reference surface area value. This is further discussed above in connection with the calculation unit.

In another embodiment of the method according to the invention, the calculating step may comprise determining the reference surface area value as a function of at least one previously measured surface area value. This is further discussed above in connection with the calculation unit.

In another embodiment of the method according to the invention, the method is further comprising the step of generating sleep status information by detecting a sleeping status of the patient, wherein the onset of at least one of the steps of the method is dependent on the sleep status information. This is further discussed above in connection with the sleep indication unit.

In another embodiment of the method according to the invention, the measuring of an impedance of the patient is initiated if the sleep status information indicates a sleeping state of the patient. This is further discussed above in connection with the sleep indication unit.

In another embodiment of the method according to the invention, the hemodynamic and/or apnea measures are calculated as a function of the sleep status information. This is further discussed above in connection with the sleep indication unit.

In an embodiment, the computer program product according to the invention may be directly loadable into an implantable medical device for causing the implantable medical device to perform the steps in accordance with the method aspect of the invention.

In the present disclosure, there is also provided an implantable medical device for detecting atrial fibrosis. Such implantable medical device includes a pulse generator adapted to produce cardiac stimulating pacing pulses, and the device is connectable to at least one medical lead comprising electrodes for delivering the pulses to cardiac tissue of a heart of a patient. Further, the device comprises: an impedance measuring unit, connectable to at least two electrodes of the at least one medical lead, adapted to measure an impedance substantially corresponding to an impedance of an atrium of the patient, and provide impedance information corresponding to the measured impedance; a cardiogenic impedance determining unit adapted to receive the impedance information and determine cardiogenic impedance data from the impedance information; a calculation unit adapted to determine at least one hemodynamic measure using the cardiogenic impedance data, wherein the hemodynamic measures can be utilized for detecting atrial fibrosis in the patient.

Different embodiments of the implantable medical device for detecting atrial fibrosis correspond to those described in connection with: the impedance measuring unit; the cardiogenic impedance determining unit; the functions of the calculation unit relating to the cardiogenic impedance data, the cardiogenic impedance curve and the hemodynamic measure; the ECG measuring unit and the sleep indication unit. Those of ordinary skill in the art may, without being inventive, transfer the teachings of the above-mentioned embodiments to the context of the implantable medical device for detecting atrial fibrosis.

DESCRIPTION OF THE PREFERRED EMBODIMENTS

Figure 1:
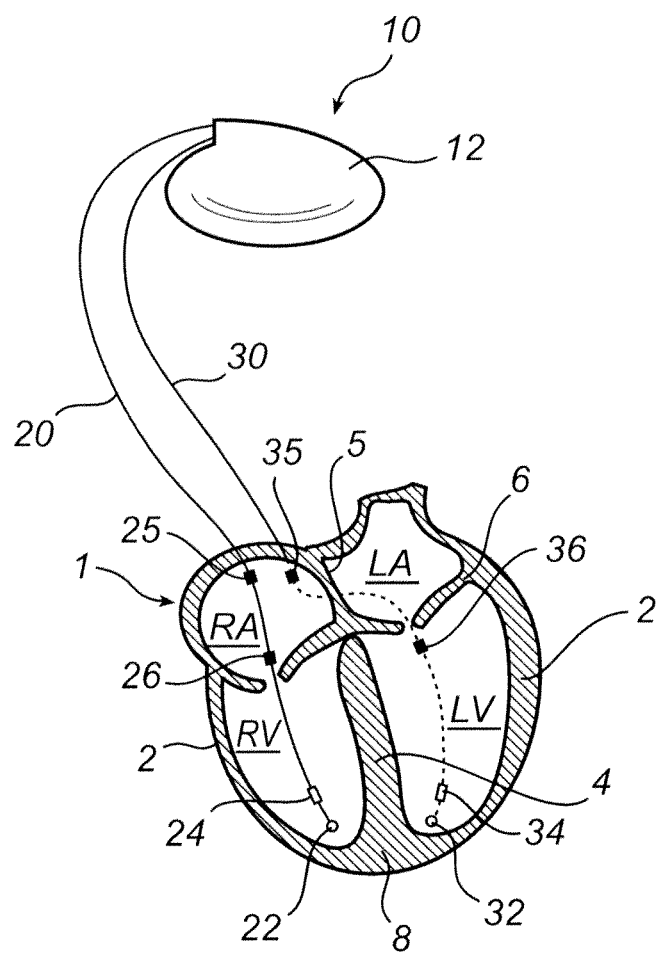
FIG. 1 is a simplified partly cutaway view illustrating an implantable medical device including an electrode configuration according to an embodiment of the present invention.

With reference first to FIG. 1, there is shown an embodiment of the present invention. A implantable medical device 10 is in electrical communication with a patient's heart 1 by way of two leads 20 and 30 suitable for delivering multi-chamber stimulation, which leads 20 and 30 are connectable to the stimulator 10. The illustrated portions of the heart 1 include right atrium RA, the right ventricle RV, the left atrium LA, the left ventricle LV, cardiac walls 2, the ventricle septum 4, the valve plane 6, and the apex 8.

In order to sense right ventricular and atrial cardiac signals and impedances and to provide stimulation therapy to the right ventricle RV, the implantable medical device 10 is coupled to an implantable right ventricular lead 20, which may have a ventricular tip electrode 22, a ventricular annular or ring electrodes 24 and 26, and/or a atrial annular or ring electrode 25. The right ventricular tip electrode 22 is arranged to be implanted in the endocardium of the right ventricle, e.g. near the apex 8 of the heart. Thereby, the tip electrode 22 becomes attached to cardiac wall. In this example, the tip electrode 22 is fixedly mounted in a distal header portion of the lead 20. Furthermore, the ventricular electrode 26, which may a annular or ring electrode, is in this embodiment located substantially at the level of the valve plane 6.

In order to sense left atrium and ventricular cardiac signals and impedances and to provide pacing therapy for the left ventricle LV, the implantable medical device 10 is coupled to a "coronary sinus" lead 30 designed for placement via the coronary sinus in veins located distally thereof, so as to place a distal electrode adjacent to the left ventricle and an electrode adjacent to the right atrium RA. The coronary sinus lead 30 is designed to receive ventricular cardiac signals from the cardiac stimulator 10 and to deliver left ventricular LV pacing therapy using at least a left ventricular tip electrode 32 to the heart 1. In the illustrated example, the LV lead 30 further comprises an annular ring electrode 34 for sensing electrical activity related to the left ventricle LV of the heart. Moreover, a second ventricular electrode 36, which may be an annular or ring electrode, may be located substantially at the level of the valve plane 6 and an atrial electrode 35, which may an annular or ring electrode, may be located in, or adjacent to, the right atrium RA.

With reference to the configuration shown in FIG. 1, a number of impedances vectors that can be used for impedance measurements will be described. For example, a quadropolar impedance measurement wherein the current is applied between the ring electrode 25 of the right atrium and the tip electrode 22 of the right ventricle, and the resulting impedance is measured between the ring electrode 26 of the right atrium and the ring electrode 24 of the right ventricle. A further alternative is a quadropolar impedance measurement vector where the current is applied between the ring electrode 25 of the right atrium and the case 12. The resulting impedance is measured between the ring electrodes 25 and 34 or 36 of the right atrium and left ventricle, respectively. Another alternative is a quadropolar impedance vector where the current is applied between the case 12 and the ring electrode 24, and the resulting impedance is measured between the ring electrodes 25 and 26. Yet another alternative is an impedance measurement vector where the current is applied between the ring electrode 25 of the right atrium and the ring electrode 34 or 36 of the left ventricle. The resulting impedance is measured between the same electrodes. As the skilled person realizes, there are a number of other conceivable measurement vectors that can be used to measure the impedance, for example, if a further medical lead is implanted in the right atrium, the current may be applied between a tip electrode of the right atrium lead and the tip electrode of the right ventricle lead and the resulting impedance can be measured between a ring electrode of the right atrium electrode and the ring electrode of the right ventricle electrode. However, in a preferred embodiment, the impedance vector is chosen so as to measure an impedance substantially corresponding to an impedance of an atrium, such as the right atrium, of the patient.

Those of skill in the art will realize that a number of different variables can be determined from the resulting impedance, which may be used to determine the hemodynamic measure. Examples are the resistance, and/or the reactance, and/or the phase angle, and/or the magnitude of the impedance, i.e. the magnitude of the impedance vector consisting of the real part (the resistance), and the imaginary part (the reactance). In embodiments, the frequency may be varied such that measurements are made at different frequencies, for example, each measurement may be performed at a number of frequencies in a frequency interval. Furthermore, the time derivative may for example be determined for the resistance, and/or the reactance, and/or the phase angle, and/or the magnitude of the impedance.

Figure 2:
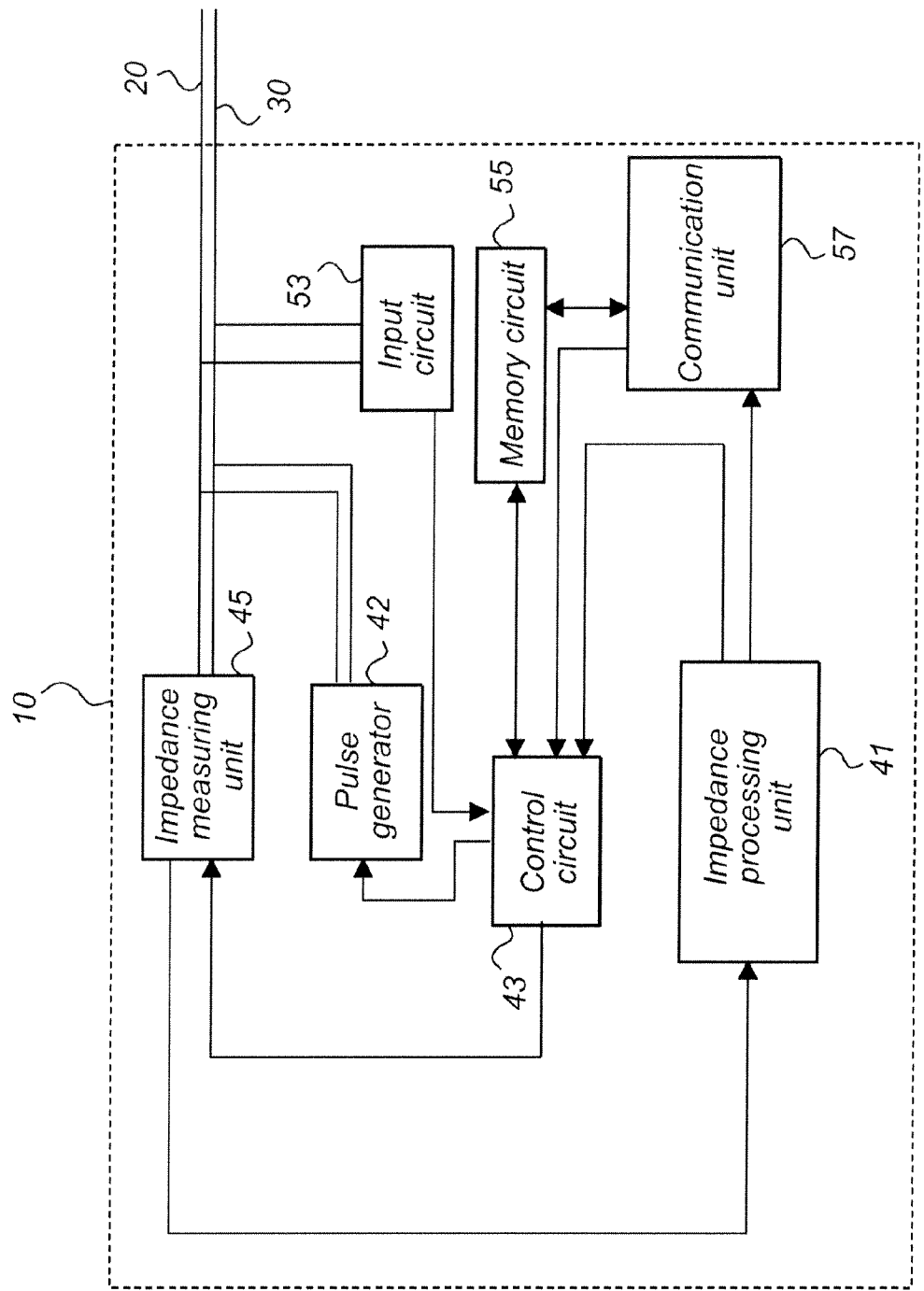
FIG. 2 is block diagram of the primary functional components of an embodiment of the implantable medical device according to the present invention.

With reference to FIG. 2, an embodiment of the implantable medical device according to the present invention will be shown. This embodiment of the present invention is implemented in the context of a implantable medical device 10 implanted in a patient (not shown). The implantable medical device 10 comprises a housing being hermetically sealed and biologically inert. Normally, the housing is conductive and may, thus, serve as an electrode. One or more pacemaker leads, where only two are shown in FIG. 1, 20 and 30, are electrically coupled to the implantable medical device 10 in a conventional manner. The leads 20, 30 extend into the heart (not shown) via a vein of the patient. One or more conductive electrodes for receiving electrical cardiac signals and impedances and/or for delivering electrical pacing to the heart are arranged near the distal ends of the leads 20, 30.

The leads 20, 30 comprises one or more electrodes, such a tip electrodes or a ring electrodes, arranged to, inter alia, transmit pacing pulses for causing depolarization of cardiac tissue adjacent to the electrode(s) generated by a pace pulse generator 42 under influence of a control circuit 43 comprising a microprocessor. The control circuit 43 controls, inter alia, pace pulse parameters such as output voltage and pulse duration. A memory circuit 55 is connected to the control circuit 43, which memory circuit 55 may include a random access memory (RAM) and/or a non-volatile memory such as a read-only memory (ROM). Detected signals from the patient's heart are processed in an input circuit 53 and are forwarded to the microprocessor of the control circuit 43 for use in logic timing determination in known manner.

Furthermore, an impedance measuring unit 45 is adapted to carry out impedance measurements of the cardiac impedance of the patient. The impedance vector used should preferably capture the filling or emptying of an atrium (right and/or left). The impedance measuring unit 45 is thus arranged to apply excitation current pulses between a first electrode and a second electrode. For example, these electrodes are arranged within a heart of the patient. With reference also to FIG. 1, in one embodiment, a current is emitted between a right atrial ring electrode 25 or 26 and the housing (case) 12 of the implantable medical device 10, and a voltage is measured between a right atrial ring electrode 25 or 26 and a left ventricular ring electrode 34 or 36.

The impedance measuring unit 45 may include an amplifier (not shown) that amplifies the evoked voltage response, i.e. the measured voltage, and may be synchronized in a multiplier with the excitation current. Thus, the impedance measuring unit 45 obtains the cardiac impedance given by the delivered current and the evoked voltage response. Then, the impedance information corresponding to the measured impedance is sent to an impedance processing unit 41.

The impedance information used may include the resistive part of the cardiac impedance. Furthermore, the impedance information may additionally or alternatively, for example, include the magnitude of the complex impedance, the real and/or imaginary part (i.e. the inductive or capacitive part) of the complex impedance.

The impedance processing unit 41 may be adapted to receive and filter the impedance information and determine cardiogenic and respiratory data, e.g. averaged data. The determination of the cardiogenic data may be based on information obtained during a time interval of a plurality of cardiac cycles or during one heart beat only, and the determination of the respiratory data may be based on information obtained during a time interval corresponding to a normal breath, or a plurality of normal breaths. Alternatively, the determinations may be based on impedance information received during a predetermined time intervals. Furthermore, a hemodynamic measure and a apnea measure are calculated from the hemodynamic and respiratory data, respectively. Different approaches for calculating these measures will be discussed below. Thereafter, the obtained measures are correlated for predicting potential occurrence of atrial fibrillation.

The control circuit 43 may be connected to the impedance processing unit 41 to control the impedance measuring unit 45 in response to output from the impedance processing unit 41 such that the impedance measurements can be optimized.

Figure 3:
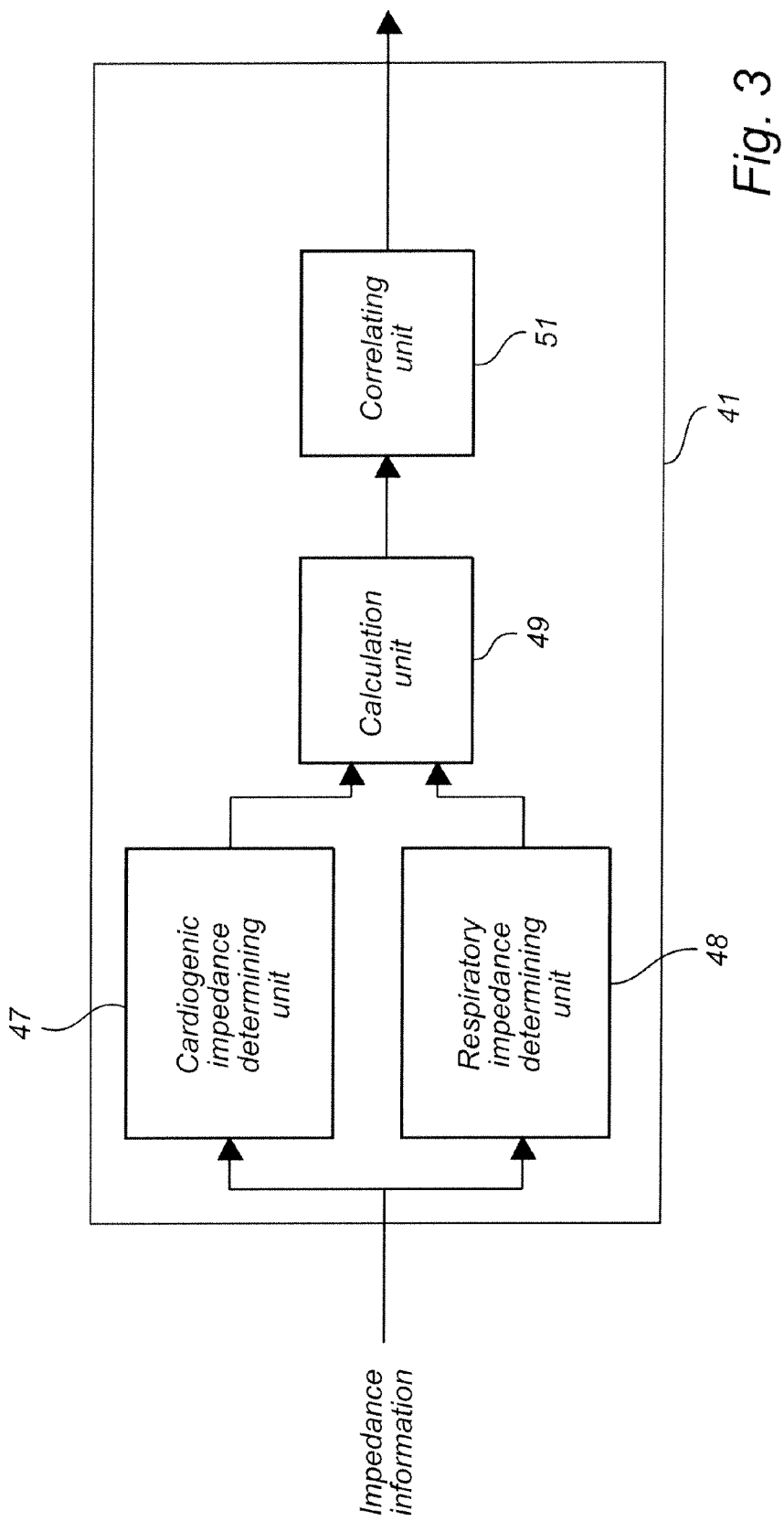
FIG. 3 is a block diagram of a part of the embodiment of the implantable medical device shown in FIG. 2.

With reference to FIG. 3, an embodiment of the impedance processing unit 41 will be described. An cardiogenic impedance determining unit 47 is adapted to receive the impedance information corresponding to impedance measured by the impedance measuring unit. The cardiogenic impedance determining unit 47 may be adapted to filter the impedance information to obtain cardiogenic specific impedance information corresponding to the heart, such as an atrium. Further, the cardiogenic impedance determining unit 47 is adapted to determine cardiogenic impedance data from the impedance information, such as from the filtered cardiogenic specific impedance information. This determination may be based on impedance information received during a time interval of a plurality of cardiac cycles or during one heart beat only. Consequently, the cardiogenic impedance data may be averaged data.

Likewise, a respiratory impedance determining unit 48 is adapted to receive the impedance information corresponding to impedance measured by the impedance measuring unit 45. The respiratory impedance determining unit 48 may be adapted to filter the impedance information to obtain respiratory specific impedance information corresponding to physical movements caused by the patients breathing, e.g. the movements of the tissues surrounding the lungs during inhaling and exhaling. Further, the respiratory impedance determining unit 47 is adapted to determine respiratory impedance data from the impedance information, such as the filtered respiratory specific impedance information. This determination may be based impedance information received during a time interval corresponding to one normal breath or a plurality of normal breaths. Alternatively, the determination may be based on impedance information received during a predetermined time interval.

The calculation unit 49 is adapted to receive the cardiogenic and respiratory impedance data from the cardiogenic impedance determining unit and respiratory impedance determining unit, respectively. Further, the calculation unit 49 may be adapted to determine a cardiogenic impedance curve by means of the cardiogenic impedance data and a respiratory impedance curve by means of the respiratory impedance data. Also, the calculation unit 49 is adapted to determine a hemodynamic measure from the cardiogenic impedance data or curve and an apnea measure from the respiratory impedance data or curve. The determination of the hemodynamic measure or the cardiogenic impedance curve may be based on cardiogenic impedance data received during a time interval of a plurality of cardiac cycles or during one heart beat only. Further, the determination of the apnea measure or the respiratory impedance curve may be based on respiratory impedance data received during a time interval corresponding to one normal breath or a plurality of normal breaths, or alternatively, during a predetermined time interval. Consequently, the hemodynamic or apnea measures may be averaged measures.

In the correlating unit 51, the hemodynamic and apnea measures are correlated so as to provide correlated measures useful for predicting potential occurrence of AF. As an example, measures may be synchronized in the correlating unit.

In one embodiment, the calculation unit 49 and/or the correlating unit 51 may be connected to a memory circuit (not shown FIG. 3). In such embodiment, the memory circuit may be adapted to receive and store hemodynamic and apnea measures from the calculation unit 49 and/or the correlated hemodynamic and apnea measures form the correlating unit 51. Further, the correlating unit may be adapted to receive hemodynamic and apnea measures, such as correlated hemodynamic and apnea measures, from the memory circuit 55. Consequently, in one embodiment, the correlating unit 51 may provide curves showing the development of the hemodynamic and apnea measures over time.

The implantable medical device 10 is powered by a battery (not shown), which supplies electrical power to all electrical active components of the medical device 10. Data contained in, for example, the memory circuit 55 can be transferred to an extracorporeal programmer (not shown in FIG. 1) via a communication unit 57, e.g. a telemetry unit. The programmer may include a programmer interface for use in an analysis the hemodynamic and apnea measures. The correlating unit 51 may also be adapted to transfer measures to the programmer via the communication unit 57. In one embodiment, the correlated measures from the correlating unit are transferred via the communication unit 57 and the extracorporeal programmer and displayed by a display device adapted to visually display the correlated hemodynamic and apnea measures.

Also, in one embodiment, the implantable medical device may include a ECG-measuring unit (not shown) connected to at least one electrode and the calculation unit. The ECG-measuring unit is adapted to receive an ECG signal from the heart of the patient, determine an ECG curve and detect a QRS complex of the ECG complex. In such embodiment, the calculation unit 49 is further adapted to obtain ECG curve and QRS complex information from the ECG-measuring unity and synchronize the QRS complex with the cardiogenic impedance curve determined as described above. Also, the calculation unit 49 is adapted to determine the hemodynamic measure from the cardiogenic impedance curve in a time window following the QRS complex. For example, the calculation unit 49 may be adapted to calculate the hemodynamic measure by means of a time derivative of the cardiogenic impedance curve in such time window.

Furthermore, in one embodiment, the implantable medical device 10 may include a sleep indication unit adapted to detect a sleeping state of the patient and generate sleep status information. In one embodiment, the sleep indication unit may be connected to a posture sensor (not shown) arranged to detect, for example, a predetermined, specific body posture of the patient. The posture detecting sensor may be connected to the control circuit and adapted to provide at least one posture indicating signal. In one embodiment, the sleep indication circuit is adapted to generate information indicating a sleeping state of the patient upon receiving a posture indicating signal that indicates that the patient is in a lying position. For example, a sleeping state may be indicated if signals indicating a lying position have been received by the sleep indication unit during a predetermined time interval, such as at least 30 minutes.

In another embodiment, the sleep indication unit may be adapted to receive breathing information corresponding to the patients breathing. As an example, the sleep indication unit may obtain breathing information from the impedance measuring unit 45 or impedance processing unit 41, such as from the respiratory impedance determining unit 48, the calculation unit 49 or the correlating unit 51. Consequently, the breathing information may e.g. be the above-mentioned impedance information, respiratory impedance data or respiratory impedance curve. As another example, the implantable medical device may comprise a breathing sensor (not shown) adapted to sense a breathing a of the patient and provide breathing information. The sleep indication unit may be adapted to determine a breathing rate, e.g. breaths per minute, from the breathing information and indicate a sleeping state if the breathing rate is within at least one predetermined interval, such as an interval being associated with a sleeping state.

In yet another embodiment, the sleep indication unit may be connected to an activity level sensor (not shown) adapted to sense an activity level of the patient and provide least one activity level indicating signal. The sleep indication unit may be adapted to receive the activity level indicating signal and indicate a sleeping state when the activity level is within at least one predetermined interval, such as an interval being associated with a sleeping state.

Further, the sleep indication unit may be connected to the impedance measuring unit 45, the impedance processing unit 41 and/or the control circuit 43. In one embodiment, the impedance measuring unit 45 may be adapted to receive sleep status information, either directly from the sleep indication unit, or indirectly, e.g. via the control circuit 43, and initiate impedance measurements if receiving sleep status information indicating a sleeping state of the patient.

In another embodiment, the impedance processing unit 41 may be adapted to receive sleep status information either directly from the sleep indication unit, or indirectly, e.g. via the control circuit 43, and determine the hemodynamic and apnea measures if receiving sleep status information indicating a sleeping state.

Figure 4:
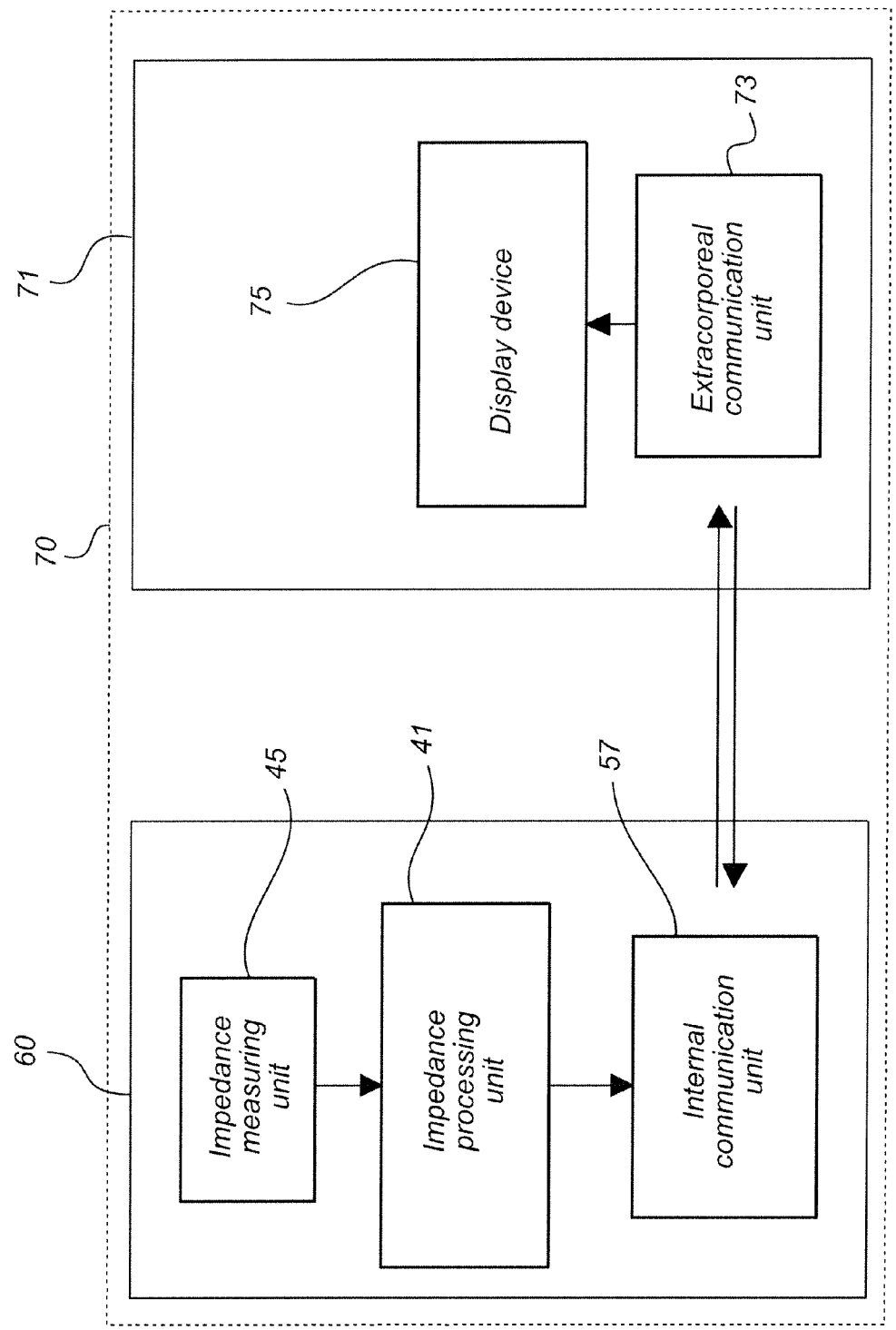
FIG. 4 is a general block diagram of an embodiment of the medical system according to the present invention.
Figure 5:
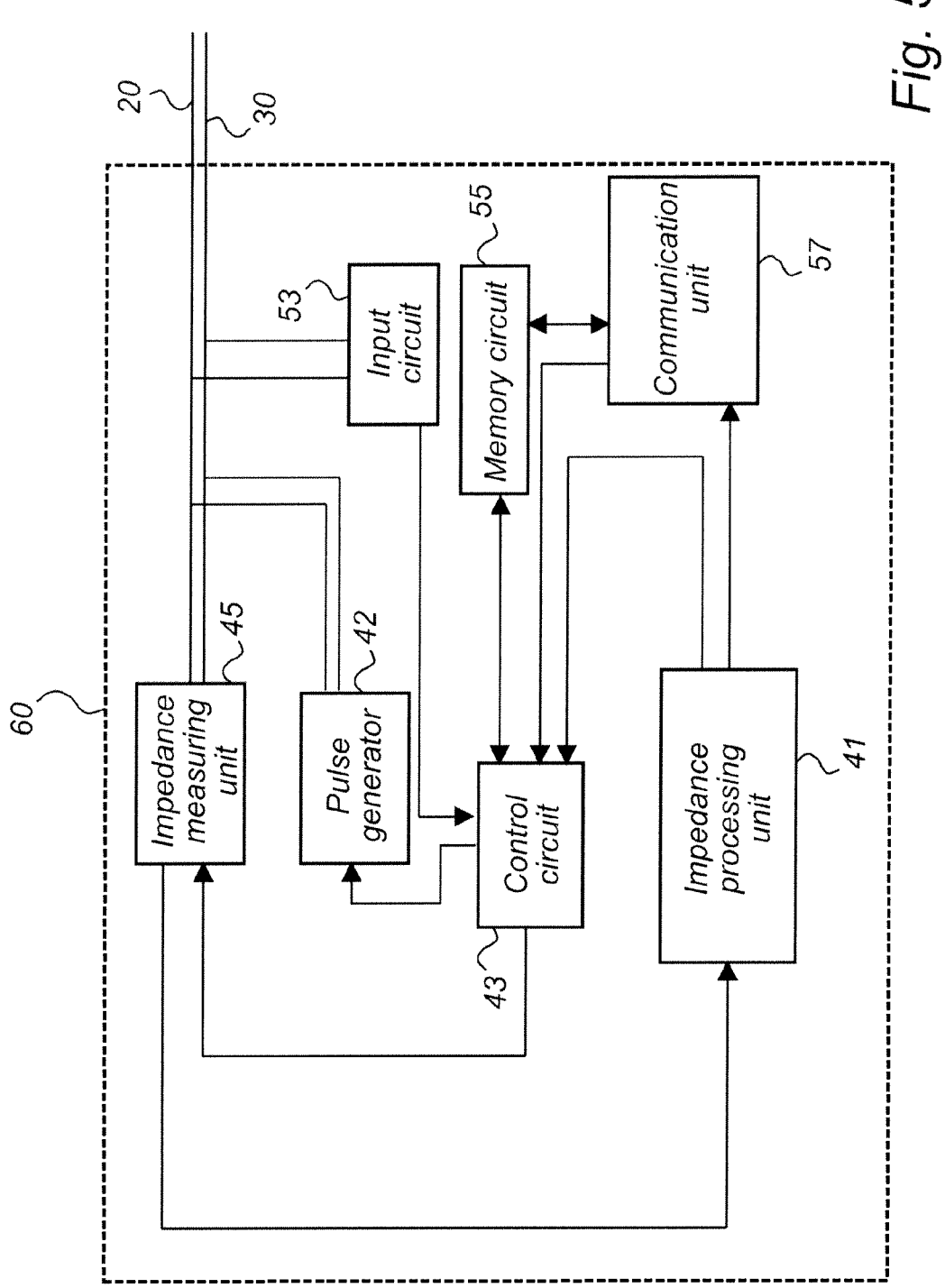
FIG. 5 is block diagram of the primary functional components of an embodiment of the implantable medical device of the medical system shown in FIG. 4 according to the present invention.
Figure 6:
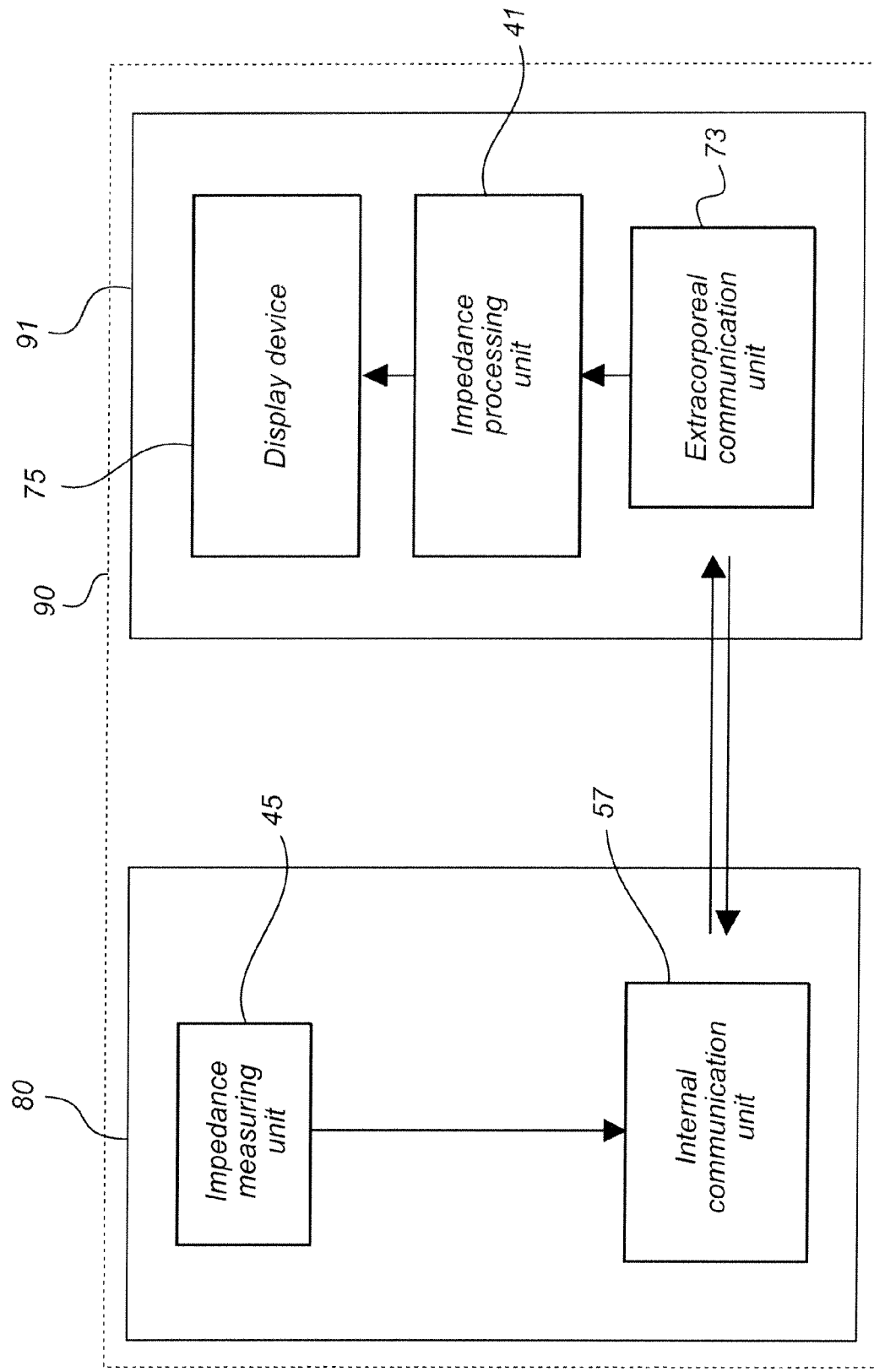
FIG. 6 is a general block diagram of another embodiment of the medical system according to the present invention.
Figure 7:
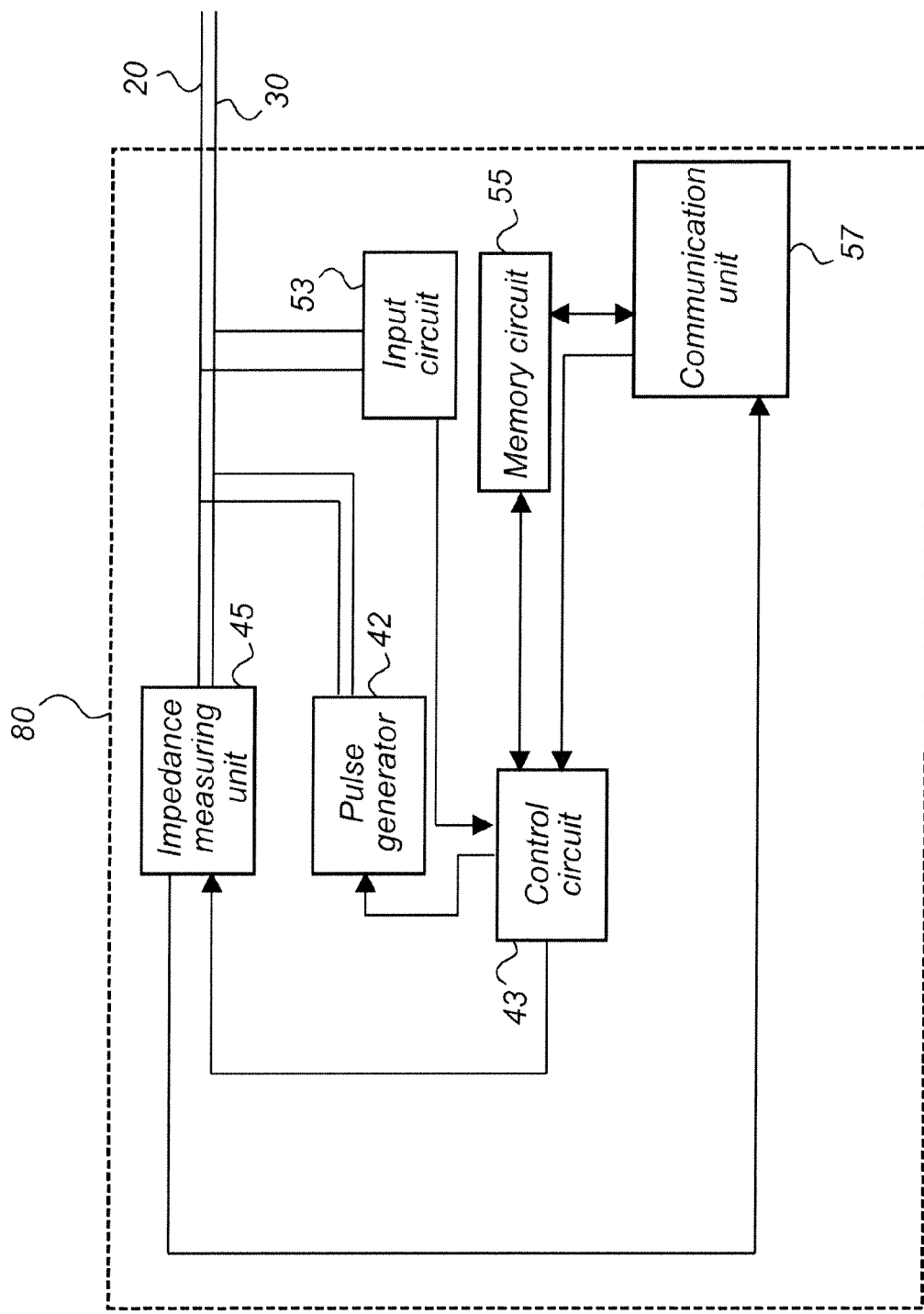
FIG. 7 is block diagram of the primary functional components of an embodiment of the implantable medical device of the medical system shown in FIG. 6 according to the present invention.
Figure 8:
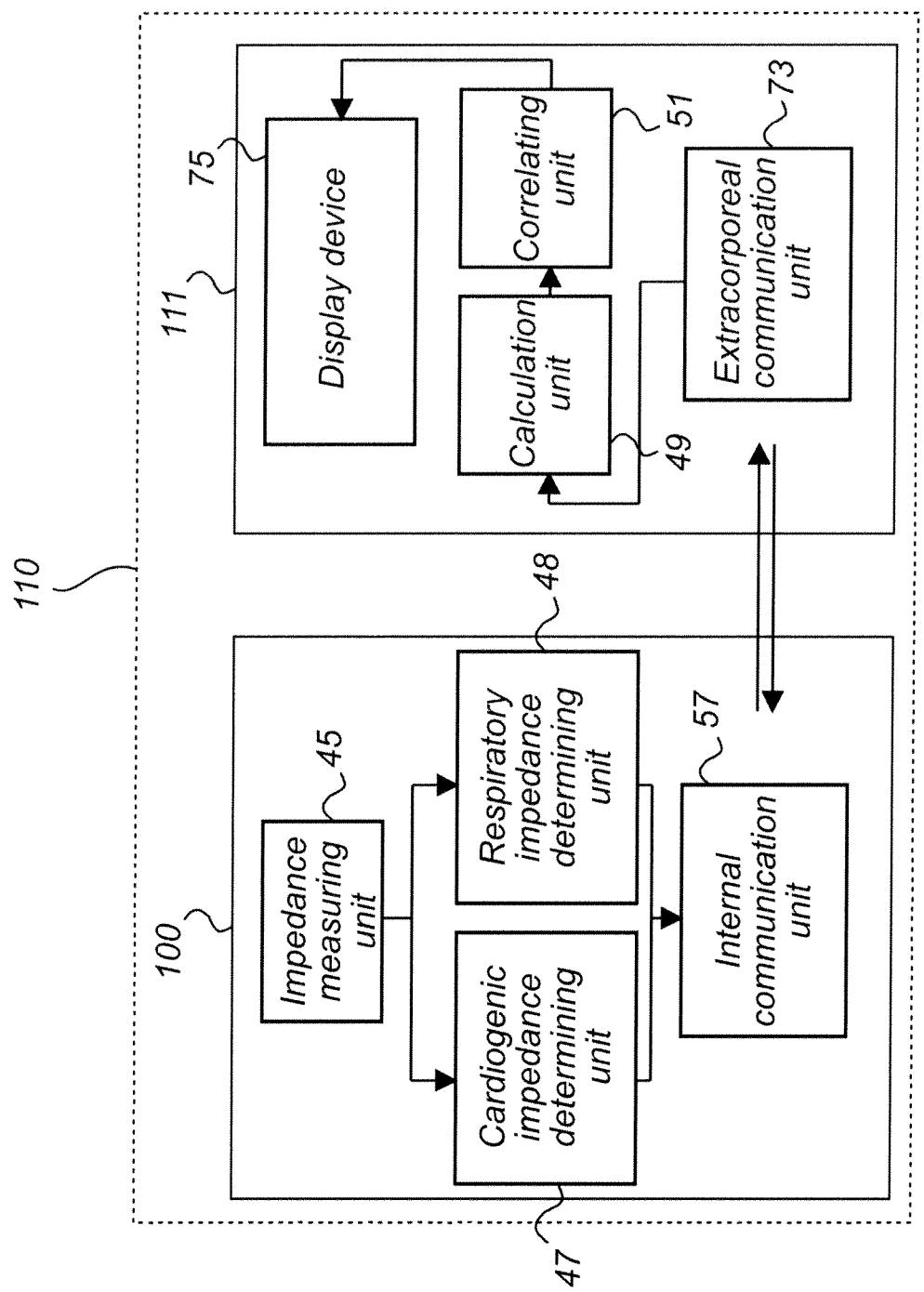
FIG. 8 is a general block diagram of another embodiment of the medical system according to the present invention.
Figure 9:
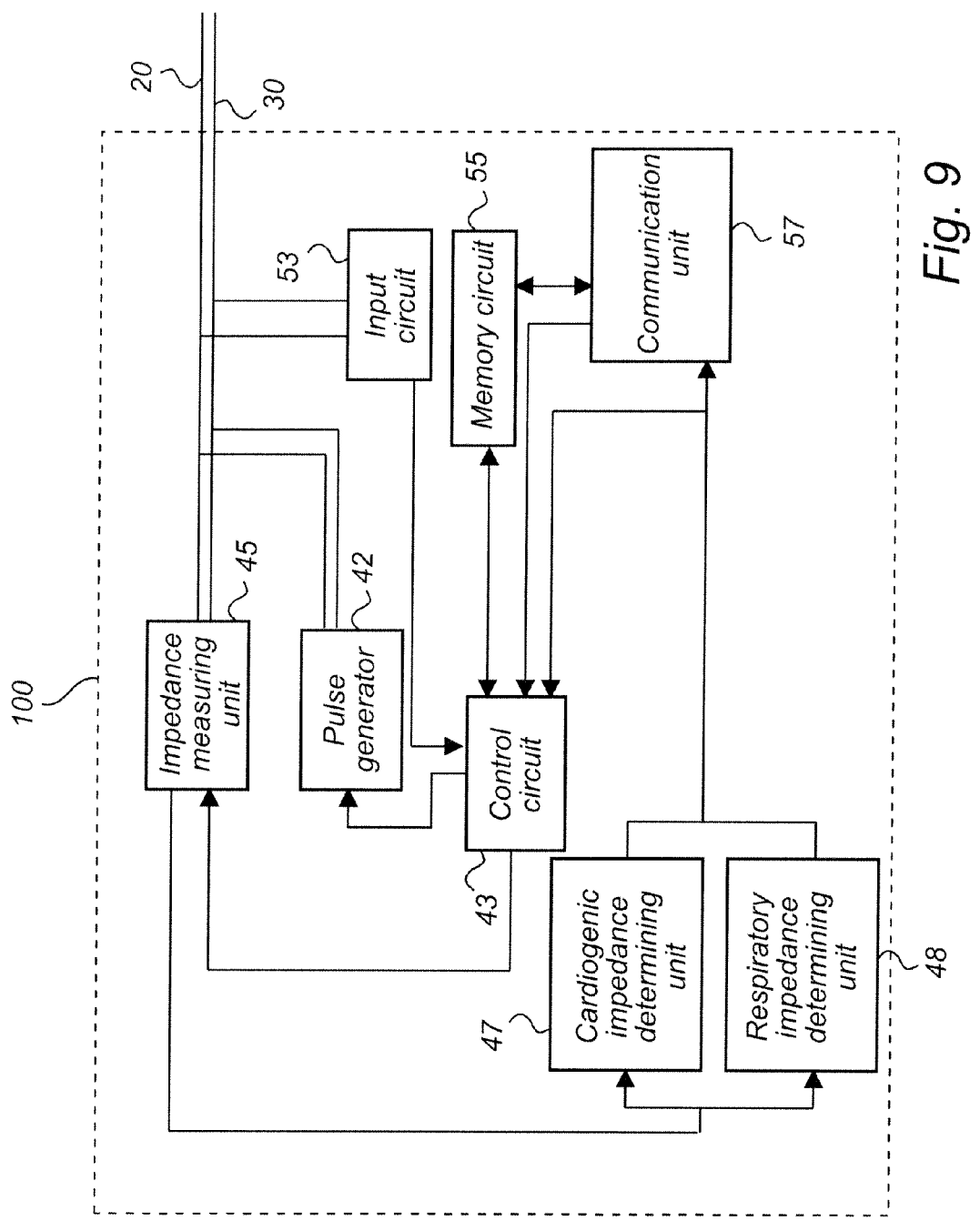
FIG. 9 is block diagram of the primary functional components of an embodiment of the implantable medical device of the medical system shown in FIG. 8 according to the present invention.

With reference now to FIGS. 4-9, embodiments of the system according to the present invention will be discussed. Like or similar parts in FIGS. 1-3, 5, 7 and 9 are denoted with the same reference numerals, and therefore the description of such parts will be omitted since they were discussed above with respect to FIGS. 1-3. Likewise, like or similar parts in FIGS. 3 and 9 are denoted with the same reference numerals and therefore the description of such parts will be omitted since they were discussed above with respect to FIG. 3.

With reference first to FIGS. 4 and 5, one embodiment of the system according to the present invention will be described. In FIG. 4, it can be seen that the system 70 includes an implantable device 60, which is shown in more detail in FIG. 4, and an extracorporeal programmer apparatus 71. The implantable device 60 and the extracorporeal programmer 71 are adapted for two-way communication between each other via the internal communication unit 57 and a extracorporeal communication unit 73, respectively. In this embodiment, the implantable medical device 60 comprises the impedance processing unit 41 adapted to receive the impedance information from the impedance measuring unit 45 and to determine correlated hemodynamic and apnea measures from the impedance information. The correlated hemodynamic and apnea measures can be stored in the memory circuit 55 or they may be buffered locally in the impedance processing unit 41 before being transferred to the extracorporeal programmer apparatus 71 via the communication units 57 and 73, respectively. This transfer can be performed either continuously or at predetermined intervals of time. The extracorporeal programmer apparatus 71, further comprises a display device 75 adapted to receive the correlated hemodynamic and apnea measures from the extracorporeal communication unit 73 and visually display them.

With reference first to FIGS. 6 and 7, one embodiment of the system according to the present invention will be described. In FIG. 6, it can be seen that the system 90 includes an implantable device 80, which is shown in more detail in FIG. 7, and an extracorporeal programmer apparatus 91. The implantable device 80 and the extracorporeal programmer 91 are adapted for two-way communication between each other via the internal communication unit 57 and a extracorporeal communication unit 73, respectively. In this embodiment, the internal communication unit 73 of the implantable medical device 80 is adapted to receive the impedance information from the impedance measuring unit 45 and transfer the impedance information to the extracorporeal programmer apparatus 91 via the communication units 57 and 73, respectively. This transfer can be performed either continuously or at predetermined intervals of time. The impedance information may be stored in the memory circuit 55 or buffered locally in the impedance measuring unit 45 before being transferred to the extracorporeal programmer apparatus 91. The extracorporeal programmer apparatus 91, comprises a impedance processing unit 41 adapted to receive the transferred impedance information from the extracorporeal communication unit 73 and determine correlated hemodynamic and apnea measures from the impedance information. As an example, the extracorporeal programmer apparatus 91 may further comprise a display device 75 adapted to receive the correlated hemodynamic and apnea measures from the impedance processing unit 41 and visually display them.

With reference first to FIGS. 8 and 9, one embodiment of the system according to the present invention will be described. In FIG. 8, it can be seen that the system 110 includes an implantable device 100 which is shown in more detail in FIG. 9, and an extracorporeal programmer apparatus 111. The implantable device 100 and the extracorporeal programmer 111 are adapted for two-way communication between each other via the internal communication unit 57 and a extracorporeal communication unit 73, respectively. In this embodiment, a cardiogenic impedance determining unit 47 and a respiratory impedance determining unit 48 are adapted to receive impedance information from the impedance measuring unit 45 and determine cardiogenic and respiratory impedance data, respectively. The internal communication unit 73 of the implantable medical device 100 is adapted to receive the cardiogenic and respiratory impedance data from the cardiogenic impedance determining unit 47 and the respiratory impedance determining unit 48, respectively, and transfer the cardiogenic and respiratory impedance data to the extracorporeal programmer apparatus 111 via the communication units 57 and 73, respectively. This transfer can be performed either continuously or at predetermined intervals of time. The cardiogenic and respiratory impedance data may be stored in the memory circuit 55 or buffered locally in the cardiogenic impedance determining unit 47 and the respiratory impedance determining unit 48, respectively, before being transferred to the extracorporeal programmer apparatus 111. The extracorporeal programmer apparatus 111, comprises a calculation unit 49 adapted to receive the transferred cardiogenic and respiratory impedance data from the extracorporeal communication unit 73 and determine hemodynamic and apnea measures from the cardiogenic and respiratory impedance data, respectively. Furthermore, the extracorporeal programmer apparatus 111, comprises a correlating unit 51 adapted to receive and correlate the hemodynamic and apnea measures for predicting potential occurrence of AF. As an example, such prediction may be assisted by a display device presenting the correlated measures. Consequently, the extracorporeal programmer apparatus 111 may further comprise a display device adapted to receive the correlated hemodynamic and apnea measures from the correlating unit 51 and visually display them.

It will be apparent to those having ordinary skill in the art that any other division of the units of the impedance processing unit 41 between an implantable device and an extracorporeal programmer apparatus also fall within the present invention. Consequently, the cardiogenic and respiratory determining units 47 and 48 and the calculation unit 49 may for example be arranged in the implantable medical device while the correlation unit is arranged in the extracorporeal programmer apparatus.

Figure 10:
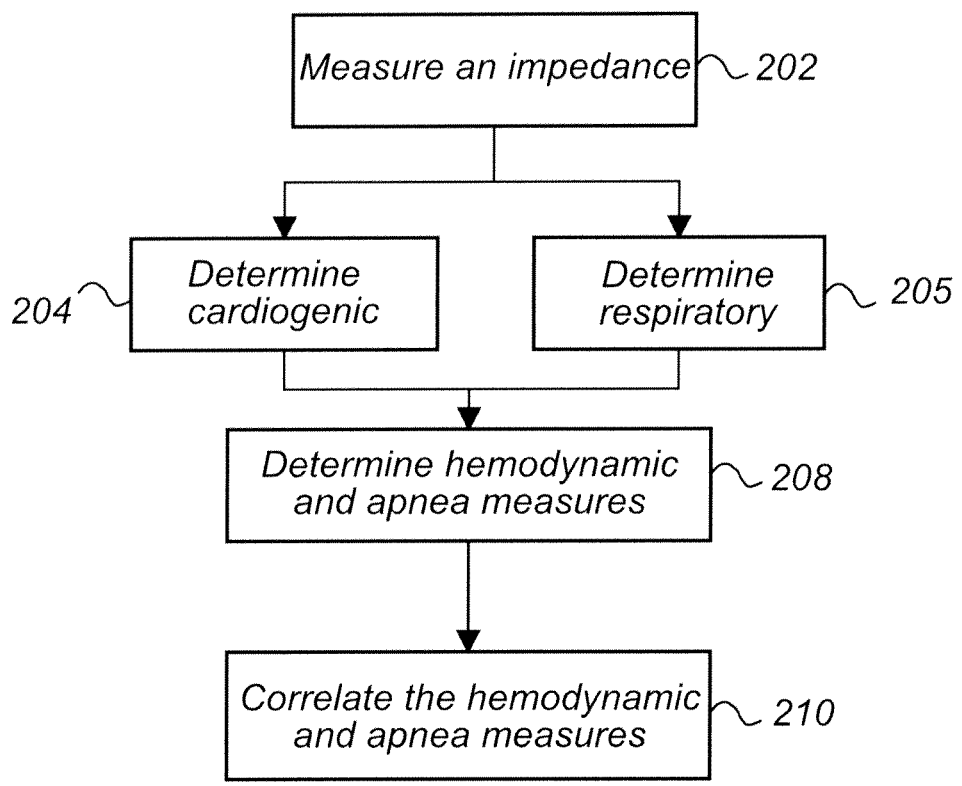
FIG. 10 is a flow chart illustrating the steps in accordance with an embodiment of the present invention for determining correlated measures for an AF prediction.

FIG. 10 shows a general description of the method for providing correlated measures for predicting potential occurrence of atrial fibrillation. First, at step 202, measurement(s) of an impedance of the patient, such as an impedance substantially corresponding to an impedance of an atrium of the patient, is performed to obtain impedance information. The impedance measurement(s) may be performed utilizing various electrodes as described above. Thereafter, at steps 204 and 205, which may be parallel, cardiogenic and respiratory data, respectively, are determined from the obtained impedance information. The determination of the cardiogenic data may be performed during a plurality of cardiac cycles or during one heartbeat only. Further, the determination of the respiratory data may be performed during a time interval corresponding to one normal breath or a plurality of normal breaths. Alternatively, the determination may be based on impedance information received during a predetermined time interval. As discussed above, these steps may be performed either in an implantable medical device or in an extracorporeal programmer apparatus. If the impedance data are determined in the programmer, the impedance information may be streamed over to the programmer from the implantable device or transferred at regular intervals. If the impedance data are calculated in the implantable device, the impedance data may be transferred on a continuous basis or at regular intervals. Then, at step 208, at least one hemodynamic measure from the cardiogenic data and at least one apnea measure from the respiratory data are determined. Different approaches for calculating these measures will be discussed below. The determination of the measures may be executed in the extracorporeal programmer device or in the implantable medical device.

Thereafter, at step 210, the obtained measures are correlated for prediction of potential occurrence of AF, i.e. the at least one hemodynamic measure and the at least one cardiogenic measure are brought into a relationship. For example, the correlating may involve that the at least one hemodynamic measure and the at least one cardiogenic measure are synchronized. For example, such synchronized measures may be stored, and stored measures entail that the development of the measures over time, such as over a predetermined time interval, may be presented. An AF prediction may then be performed based on such presentation. In one embodiment, the correlating may also involve the calculation of an AF prediction value R as discussed above. Step 210 may be executed in the extracorporeal programmer device or in the implantable medical device.

Figure 11:
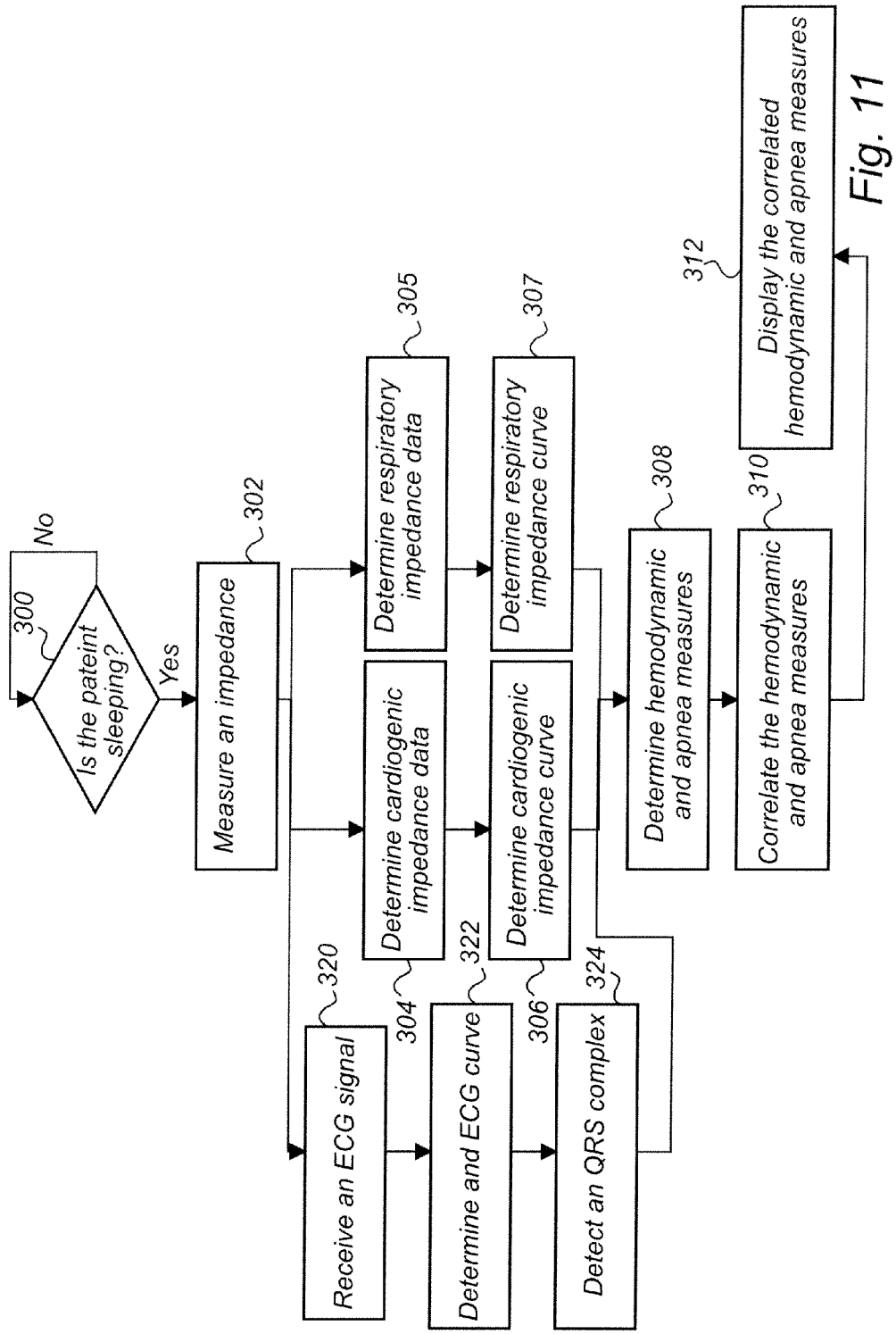
FIG. 11 is a flow chart illustrating the steps in accordance with another embodiment of the present invention for determining correlated measures for an AF prediction.

Referring now to FIG. 11, one embodiment of the method according to the invention will be discussed. First, at step 300, it may be checked whether at least one predetermined measurement criteria is met, for example, whether the patient is in a sleeping state. Different approaches for determining the sleep status of the patient are discussed above in connection with the sleep indication unit. If the patient is found not to fulfill one or more measurement criteria, e.g. if a sleeping state is not detected, the check may be performed again after a predetermined time period, such as after a time period of at least 300 seconds, such as 600 seconds. If a predetermined number of the criteria are fulfilled, measurement(s) of an impedance of the patient is performed in step 302. This step is discussed above with reference to step 202. The impedance measurements may be performed as long as the predetermined number of the measurement criteria is met, e.g. as long as the patient is sleeping. Consequently, in one embodiment, step 300 may be repeated after a predetermined time period, such as after a time period of at least 300 seconds, such as 600 seconds.

At step 305, respiratory impedance data are determined as discussed above with reference to step 205. Thereafter, at step 307, a respiratory impedance curve may be determined from the respiratory impedance data. Steps 305 and 307 may be continuously performed as long as the impedance measurement step 302 is performed or as long as the predetermined number of the measurement criteria is met. Further, at step 308, at least one apnea measure is determined from the respiratory impedance curve. Approaches for determining the at least one apnea measure is discussed below in connection with FIG. 12.

At step 304, respiratory impedance data are determined as discussed above with reference to step 204. Thereafter, at step 306, a cardiogenic impedance curve may be determined from the cardiogenic impedance data. Further, in one embodiment, ECG measurements are also performed. At step 320, an ECG signal is received from the heart of the patient, and at step 322, an ECG curve is determined from the ECG signal. Thereafter, a QRS complex of the ECG curve is detected at step 324. The steps 322 and 324 may be executed in the extracorporeal programmer device or in the implantable medical device. If the steps 322 and 324 are executed in the programmer, the ECG signal may be streamed over to the programmer from the implantable device or may be transferred at regular intervals. The steps 304, 306, 320, 322 and 324 may be performed at predetermined time intervals, such as at least 900 seconds, such as 1800 seconds, as long as the impedance measurement step 302 is performed or as long as the predetermined number of the measurement criteria is met. Further, at step 308, the at least one hemodynamic measure is calculated using the cardiogenic impedance curve from step 306. If steps 320-324 are performed, the information related to the ECG curve and/or the QRS complex may also be used in the calculation of the at least one hemodynamic measure. Approaches for determining the at least one apnea measure is discussed below in connection with FIG. 12.

At step 310, the hemodynamic and apnea measures from step 308 are correlated for prediction of potential occurrence of AF. This step is discussed above with reference to step 210. Thereafter, the correlated hemodynamic and apnea measures may be visually displayed at step 312. In an embodiment, the historic development of the measures is displayed on a common time axis, so that coinciding trends may be observed by a person watching the display. For example, from such a display, a physician may be able to observe decreasing hemodynamic measures, corresponding to a decreasing elasticity of the atrial myocardium, that coincide with increasing apnea measures, corresponding to an increasing apnea activity, and conclude that the patient is at risk of developing AF. In another embodiment, correlating the hemodynamic and apnea measures at step 310 may involve calculation of an AF prediction value, such as the AF prediction value R discussed above. The historic development of the AF prediction value may then be displayed at step 312.

Figure 12:
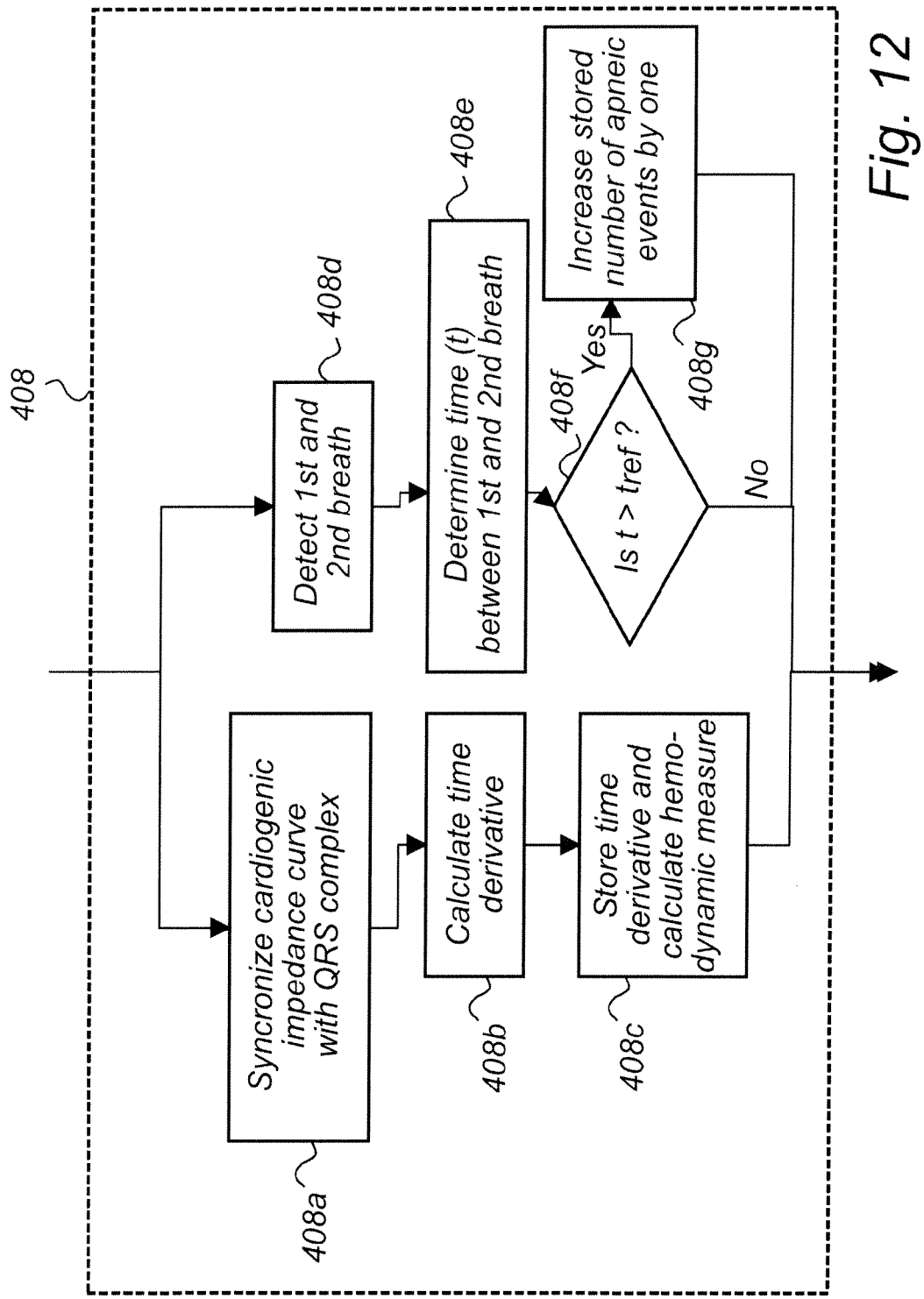
FIG. 12 is a detailed flow chart illustrating one of the steps of the embodiment of the present invention shown in FIG. 12.

Turning now to FIG. 12 showing step 408, which is a more detailed description of step 308 in FIG. 11. In this embodiment, at step 408a, the cardiogenic impedance curve obtained in step 306 is synchronized with the QRS complex detected in step 324. Thereafter, at step 408b, a time derivative of the cardiogenic impedance curve is calculated in a time window, such as a predetermined time window, following the QRS complex. This time derivative is then stored at step 408c. One single time derivative or a mean or median value of a plurality time derivatives obtained during a time period may then represent the hemodynamic measure. For example, the time period may be a predetermined time period. Alternatively, the time period may be one night of sleep, e.g. an unbroken time period of fulfilling the predetermined at least one measurement criteria or a plurality of such periods following shortly on each other.

At step 408d, a first breath and a second breath detected from the respiratory impedance curve obtained from step 307. In one embodiment, the detection of the breaths comprises integrations over peaks of the respiratory impedance curve to obtain surface area values corresponding to the peaks. The surface area values are then compared with a reference value, and if a surface area value is bigger than a reference value, the corresponding peak is detected as a breath. At step 408e, the time (t) between the first and the following second breath is calculated. Thereafter, t is compared to a reference value $t_{ref}$ at step 408f. If t is bigger than $t_{ref}$, an apneic event is considered to be detected and a stored number of apneic events are increased by one. The number of apneic events detected during a time period may then represent the apnea measure. For example, the time period may be a predetermined time period. Alternatively, the time period may be one night of sleep, e.g. an unbroken time period of fulfilling the predetermined at least one measurement criteria or a plurality of such periods following shortly on each other.

In one embodiment, one hemodynamic measure and one apnea measure per night are stored such that the development over time of these measures may be presented.

Most of the above-mentioned steps of the embodiments of the method aspect, i.e. steps 204, 205, 208, 210, 300, 304, 305, 306, 307, 308, 310, 322, 324, 408a, 408b, 408c, 408d, 408e, 408f and/or 408g, may be performed in an implantable medical device or in an extracorporeal programmer device.

Figure 13:
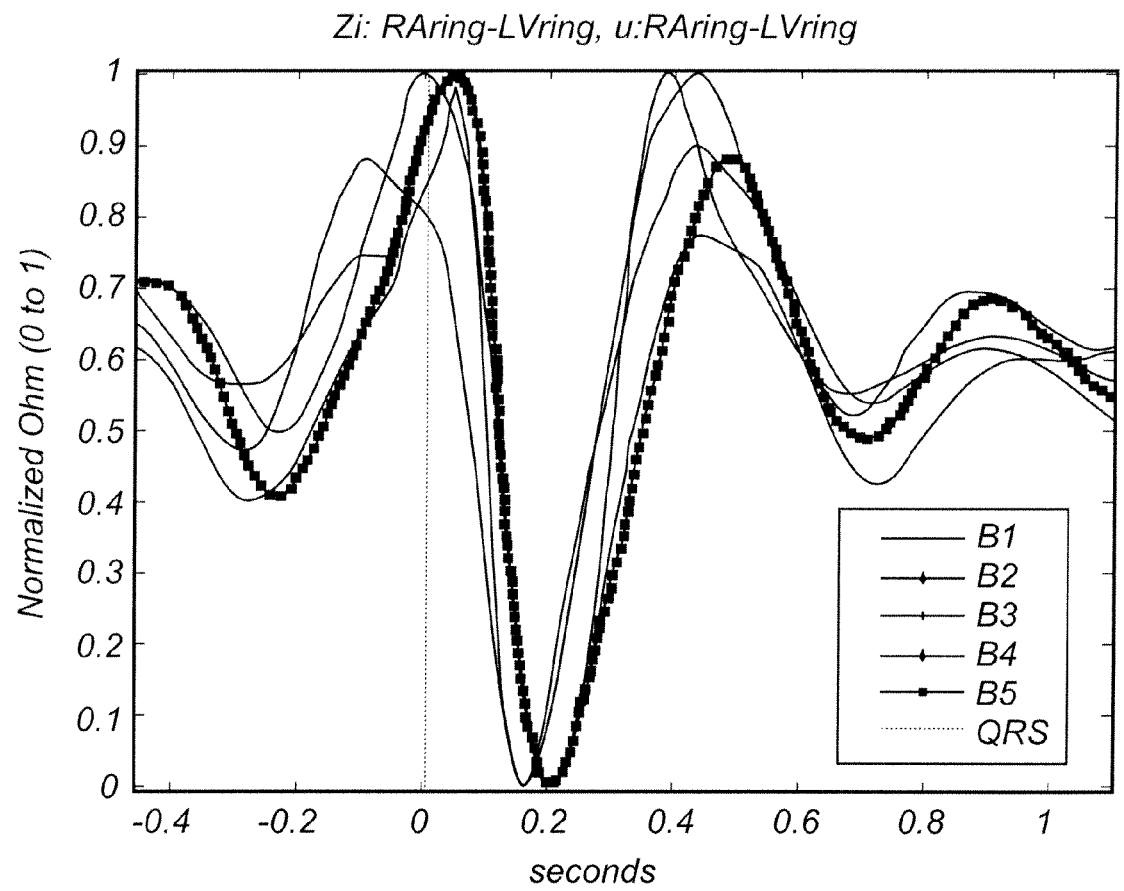
FIG. 13 shows cardiogenic impedance curves formed from impedances measured in measured in five dogs (B1-B5) with implanted Unity CRT-D devices. In this impedance measurements, the current was applied between an $RA_{ring}$ and an $LV_{ring}$ and the voltage which was measured between an $RA_{ring}$ and an $LV_{ring}$. On the time axis, t=0 corresponds to a QRS complex of an ECG signal from the right ventricle. The curves are normalized with regard to the amplitudes.

With reference to FIG. 13, a signal containing information of the blood flow in the atria may be obtained if the impedance is measured between a left ventricular coronary sinus lead and a right atrial lead, e.g. a current is applied between an $RA_{ring}$ and an $LV_{ring}$ and a voltage which is measured between an $RA_{ring}$ and an $LV_{ring}$. With such lead configuration, a drop in impedance may be observed in a time window following the QRS. The drop, or impedance decrease, indicates an increasing volume, which leads to the conclusion that the impedance of an atrium is measured with the configuration, because the atria are filled after the QRS. This drop (negative slope) may quantified by measuring the time derivative of the cardiogenic impedance curve in the time window according to steps 408a and 408b above. The time derivative reflects the speed of the filling of the atrium. A stiffer atrium, or less elastic atrial myocardium, may affect such speed, e.g. a stiffer atrium results in slower filling. Consequently, the hemodynamic measure may be calculated as a function of at least one such time derivative.

Although exemplary embodiments of the present invention have been shown and described, it will be apparent to those having ordinary skill in the art that a number of changes, modifications, or alterations to the inventions as described herein may be made. Thus, it is to be understood that the above description of the invention and the accompanying drawings is to be regarded as non-limiting examples thereof, and that the scope of protection is defined by the appended claims.

I claim as my invention:

1. An implantable medical device including a pulse generator adapted to produce cardiac stimulating pacing pulses, said device being connectable to at least one medical lead comprising electrodes for delivering said pulses to cardiac tissue of a heart of a patient, comprising:
- an impedance measuring unit, connectable to at least two electrodes of said at least one medical lead, configured to measure an impedance of said patient and to provide impedance information corresponding to said measured impedance;
- a cardiogenic impedance determining unit configured to receive said impedance information and to determine cardiogenic impedance data from said impedance information;
- a respiration impedance determining unit configured to receive said impedance information and to determine respiratory impedance data from said respiratory impedance information;
- a calculation unit configured to determine at least one hemodynamic measure using said cardiogenic impedance data and at least one apnea measure using said respiratory impedance data; and
- a correlating unit configured to calculate an atrial fibrillation prediction value as a function of a correlation between said hemodynamic and apnea measures, the correlation constituting a relationship, over a time period, between a development of said hemodynamic and apnea measures.

2. The device according to claim 1, wherein said impedance measuring unit measures a cardiogenic impedance substantially corresponding to an impedance of an atrium of said patient.

3. The device according to claim 2, wherein said correlating unit is configured to correlate said hemodynamic and apnea measures such that an increasing apnea activity of said patient coinciding with a decreasing elasticity of an atrial myocardium of said patient can be detected from said correlation.

4. The device according to claim 1, wherein said calculation unit is configured to determine said at least one hemodynamic measure as a time derivative of a cardiogenic impedance curve formed by means of said cardiogenic impedance data, said time derivative corresponding to a change of the cardiogenic impedance during a cardiac cycle.

5. The device according to claim 4, further comprising an ECG-measuring unit, connectable to at least one electrode, configured to
- receive an ECG signal from said heart,
- determine an ECG curve, and
- detect a QRS complex of said ECG curve, and wherein said calculation unit is adapted to obtain information related to said QRS complex and said ECG curve from said ECG-measuring unit,
- synchronize said cardiogenic impedance curve with said detected QRS complex, and
- calculate said time derivative in a time window following said QRS complex.

6. The device according to claim 1, wherein said calculation unit is configured to compare said hemodynamic measure with a hemodynamic reference value.

7. The device according to claim 1, wherein said apnea measure is a number of apneic events and said calculation unit is configured to detect a first breath from said respiratory impedance data and increase the said number of apneic events if no second breath is detected from said respiratory data in a time window of a predetermined length following said first breath.

8. The device according to claim 7, wherein said calculation unit is configured to detect a breath from said respiratory impedance data by integrating a respiratory impedance curve, formed by means of said respiratory data, to obtain an area value under the impedance curve.

9. The device according to claim 8, wherein said calculation unit is configured to integrate said respiratory impedance curve in a time window thereof corresponding to a substantial change in the respiratory impedance to obtain said area value.

10. The device according to claim 8, wherein said calculation unit is configured to detect said breath when said area value is higher than a reference area value.

11. The device according to claim 10, wherein said calculation unit is configured to determine the reference area value as a function of at least one measured area value.

12. The device according to claim 1, further comprising a sleep indication unit that detects a sleeping state of said patient and generates sleep status information, and wherein at least one component of said device receives said sleep status information and executes a predetermined action as a result of the received sleep status information.

13. The device according to claim 12, wherein said impedance measuring unit receives said sleep status information and initiates impedance measurements if said sleep status information indicates that said patient is sleeping.

14. The device according to claim 12, wherein said calculation unit receives said sleep status information and correlates said hemodynamic and apnea measures as a function of said sleep status information.

15. The device according to claim 1, wherein the correlation unit configures the relationship between the hemodynamic and apnea measures to be displayed as a historic development over a common time axis.

16. The device according to claim 1 further comprising memory configured to store the hemodynamic measures and the apnea measures for each night over the time period, the correlation unit configured to formulate the correlation such that the development over time of the hemodynamic and apnea measures can be presented to a person.

17. The device according to claim 1, wherein the correlation unit synchronizes the hemodynamic measures and apnea measures over a common time interval.

18. The device according to claim 1, wherein the relationship of the correlation is configured to enable the hemodynamic and apnea measures to be displayed on a common time axis such that coinciding trends are observable by a person.

* * * * *